(12) United States Patent
Fujinami et al.

(10) Patent No.: US 6,248,905 B1
(45) Date of Patent: Jun. 19, 2001

(54) ACYL DERIVATIVES OF GLYCOSYL-L-ASCORBIC ACID

(75) Inventors: Yoshihito Fujinami; Shino Okazaki; Akihiro Tai; Kenji Sasaki, all of Okayama; Itaru Yamamoto, 1-102, Kikyo-machi, Hanajiri, Okayama, all of (JP)

(73) Assignees: Kabushiki Kaisha Hayashibara Seibutsu Kagaku Kenkyujo; Itaru Yamamoto, both of Okayama (JP)

( * ) Notice: Subject to any disclaimer, the term of this patent is extended or adjusted under 35 U.S.C. 154(b) by 0 days.

(21) Appl. No.: 09/261,160

(22) Filed: Mar. 3, 1999

(30) Foreign Application Priority Data

Mar. 31, 1998 (JP) .................................. 10-101855

(51) Int. Cl.$^7$ .......................... C07D 305/12; A61K 31/34
(52) U.S. Cl. ............................. 549/315; 514/474
(58) Field of Search .............................. 549/315; 514/474

(56) References Cited

U.S. PATENT DOCUMENTS

| 5,122,536 | 6/1992 | Perricone | 514/474 |
| 5,658,957 | * 8/1997 | Martin | 514/724 |
| 5,767,095 | * 6/1998 | Winget | 514/25 |
| 5,891,452 | * 4/1999 | Sebillote-Arnaud et al. | 424/401 |

FOREIGN PATENT DOCUMENTS

| 0398484 | 11/1990 | (EP) . |
| 0425066 | 5/1991 | (EP) . |
| 0627441 | 12/1994 | (EP) . |
| 0425066 | 5/1995 | (EP) . |
| 2715565 | 8/1995 | (FR) . |
| 6228183 | 8/1994 | (JP) . |
| 6263790 | 9/1994 | (JP) . |
| 9742960 | 11/1997 | (WO) . |

OTHER PUBLICATIONS

Summary of 118th Pharmaceutical Society of Japan, Kyoto, Japan, published on Mar. 5, 1998.

Yamamoto, I. et al., "Antiscorbutic Activity of L–Ascorbic Acid 2–Glucoside and Its Availability as a Vitamin C Supplement in Normal Rats and Guinea Pigs," J. Pharmacobio–Dyn., 13,688–695(1990).

Szarek et al., "Conjugation of L–ascorbic acid and D–glucose", *Carbohydr. Res.*, vol. 67, pp. C13–C16, (1978).

* cited by examiner

*Primary Examiner*—Cecilia Tsang
*Assistant Examiner*—L. Eric Crane
(74) *Attorney, Agent, or Firm*—Browdy and Neimark

(57) ABSTRACT

Acyl derivatives of glycosyl-L-ascorbic acids which have a higher oil-solubility than L-ascorbic acid, glycosyl-L-ascorbic acids, and inorganic esters of L-ascorbic acid such as phosphates and sulfates of L-ascorbic acid. When administered to living bodies, the acyl derivatives easily permeate into living tissues to release L-ascorbic acid, resulting in an exertion of the physiological action inherent to L-ascorbic acid. Thus, the derivatives can be arbitrarily used in food products, cosmetics, and pharmaceuticals.

19 Claims, 8 Drawing Sheets

ACYL DERIVATIVES OF GLYCOSYL-L-ASCORBIC ACID

BACKGROUND OF THE INVENTION

1. Field of the Invention

The present invention relates to an oil-soluble derivative of a glycosyl-L-ascorbic acid, and more particularly to an acyl derivative of a glycosyl-L-ascorbic acid.

2. Description of the Prior Art

Vitamin C or L-ascorbic acid, an anti-scorbutus factor, has been widely used as a specific medicine for scorbutus. At present, it is revealed that vitamin C deeply correlates to hydroxyl reactions in vivo, for example, the biosynthesis of collagen, the metabolism of aromatic amino acids, and the formation of adrenalin in the adrenal; and it also plays an important role in the detoxification system for external invaders in the liver. Because of these diversified physiological activities, a quantity of L-ascorbic acid is consumed annually in the food-, cosmetic-, and pharmaceutical-fields.

As it is well known, unlike other vitamins, L-ascorbic acid is a relatively-highly unstable substance easily decomposed or denatured by heat, light, oxygen, metal ions, etc. Therefore, users must use L-ascorbic acid in a higher amount that far exceeds a theoretical level, and must pay close attention to the storing and handling of the compound. Also there exists a problem that L-ascorbic acid could not reach the desired tissues in a desired effective amount because it is not oil-soluble and the permeation to the tissues is inhibited by fat components when applied to in vivo tissues such as skin and mucosas rich in fat components. To overcome these drawbacks, many efforts have been made to convert L-ascorbic acid into its acid esters and glycosyl compounds.

Although conventional fatty acid esters such as 2-stearyl-L-ascorbic acid, 6-palmityl-L-ascorbic acid, and 2,6-dipalmityl-L-ascorbic acid have an improved oil-solubility oven intact L-ascorbic acid, these esters do not release L-ascorbic acid in vivo and could not exert the important physiological actions of L-ascorbic acid. Similar to intact L-ascorbic acid, inorganic esters of L-ascorbic acid such as phosphates and sulfates of L-ascorbic acid have the following problems; they are not oil-soluble, and in particular, these sulfates and fatty acid esters do not release L-ascorbic acid in vivo.

Glycosyl-L-ascorbic acids such as 2-O-glucopyranosyl-L-ascorbic acid and 2-O-galactopyranosyl-L-ascorbic acid, as disclosed in Japanese Patent Kokai Nos. 139,288/91, 135,992/91, 183,492/91, 228,183/94, and 263,790/94, are substances that were explored to overcome the drawbacks of L-ascorbic acid. These L-ascorbic acid derivatives have no reducing group within their molecules so that they have an extremely-high tolerance to heat, light, oxygen, and metal ions, and have a character of easily releasing L-ascorbic acid in vivo. Depending on use, the conventional L-ascorbic acid derivatives, however, have drawbacks similar to L-ascorbic acid due to their non-oil-solubility.

L-Ascorbic acid is a natural compound distributed widely in plants and animals, and is present in animals' adrenals and citrus fruits, and therefore it can be advantageously used in food products, cosmetics, and pharmaceuticals with lesser side effects. Recently, radicals formed in living bodies are known as a factor for life-style related diseases or geriatric diseases, in this regards L-ascorbic acid is said to have an activity of entrapping radicals in vivo and is capable of preventing the generation of tumor cells. It is highly speculated that the demands and uses of L-ascorbic acid will be widened more and more.

SUMMARY OF THE INVENTION

In view of the foregoing, the object of the present invention is to provide an oil-soluble substance that releases L-ascorbic acid in vivo, a process for producing the same, and uses thereof.

The present inventors continuously studied to solve the above object. As a result, they found that acyl derivatives of glycosyl-L-ascorbic acids are oil-soluble and capable of smoothly releasing L-ascorbic acid in vivo. They also found that the acyl derivatives can be easily produced in the desired amount by reacting glycosyl-L-ascorbic acids with acylating agents, and confirmed that the derivatives can be arbitrarily used in the fields of food products, cosmetics, and pharmaceuticals because of their outstanding properties. Thus, the present inventors accomplished this invention.

The present invention solves the above object by providing acyl derivatives of glycosyl-L-ascorbic acids.

The present invention solves the above object by providing a process for producing acyl derivatives of glycosyl-L-ascorbic acids, characterized in that it comprises a step of reacting glycosyl-L-ascorbic acids with acylating agents.

The present invention solves the above object by providing food products which contain the acyl derivatives of glycosyl-L-ascorbic acids.

The present invention solves the above object by providing cosmetics which contain the acyl derivatives of glycosyl-L-ascorbic acids.

The present invention solves the above object by providing pharmaceutical compositions for L-ascorbic acid-susceptive diseases, which contain the acyl derivatives of glycosyl-L-ascorbic acids.

BRIEF EXPLANATION OF THE ACCOMPANYING DRAWINGS

EXPLANATION OF SYMBOLS

Figure 1:
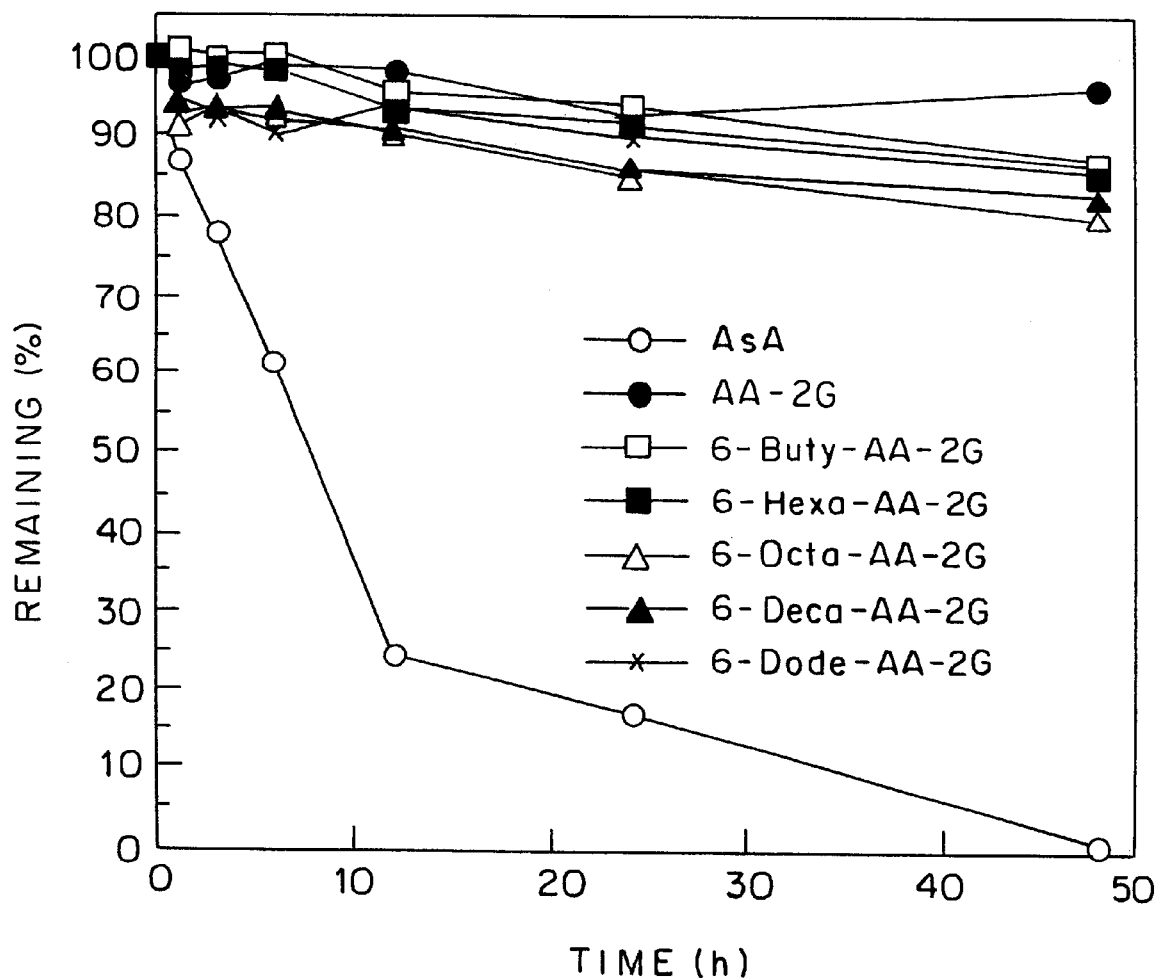
FIG. 1 is a figure that shows the stability of L-ascorbic acid, 2-O-α-D-monoglucopyranosyl-L-ascorbic acid, and the present acyl derivative in an aqueous solution at 60° C.

AsA: L-Ascorbic acid
AA 2G: 2-O-α-D-Monoglucopyranosyl-L-ascorbic acid
6-Buty-AA-2G: 6-O-Butyryl-2-O-α-D-monoglucopyranosyl-L-ascorbic acid
6-Hexa-AA-2G: 2-O-α-D-Monoglucopyranosyl-6-O-hexanoyl-L-ascorbic acid
6-Octa-AA-2G: 2-O-α-D-Monoglucopyranosyl-6-O-octanoyl-L-ascorbic acid
6-Deca-AA-2G: 6-O-Decanoyl-2-O-α-D-monoglucopyranosyl-L-ascorbic acid
6-Dode-AA-2G: 6-O-Dodecanoyl-2-O-α-D-monoglucopyranosyl-L-ascorbic acid

DETAILED DESCRIPTION OF THE INVENTION

The glycosyl-L-ascorbic acids as referred to in the present invention include all glycosyl-L-ascorbic acids wherein the oil-solubility can be improved by acylation. Preferable examples of such compounds are 2-glucopyranosyl-L-ascorbic acids including 2-O-α-D-monoglucopyranosyl-L-ascorbic acid, and 2-galactopyranosyl-L-ascorbic acids including 2-O-β-D-monogalactopyranosyl-L-ascorbic acid, which have one or more glucosyl or galactosyl residues bound to C-2 of L-ascorbic acid.

The acylation as referred to in the present invention means to introduce an acyl group or RCO— into the glycosyl-L-ascorbic acids where R represents a saturated or unsaturated straight or branched alkyl group having carbon atoms of an integer selected from 2–19 in general, and preferably from 4–17. Thus the acyl derivatives as referred to in the present invention mean the compounds in general where acyl groups are bound to one or more hydroxyl groups in the glycosyl-L-ascorbic acids, or preferably bound to one or more hydroxyl groups in an L-ascorbic acid residue.

These acyl derivatives can be prepared by different methods; they are easily obtained in a desired amount by reacting glycosyl-L-ascorbic acids with appropriate acylating agents. In this case, if necessary, catalysts can be used in the reaction system. The catalysts can be enzymes such as lipase. The glycosyl-L-ascorbic acids used as materials in the present invention can be prepared, for example, by reacting L-ascorbic acid with α-glucosyl compounds such as cyclomaltodextrins or starch hydrolysates in the presence of saccharide-transforming enzymes such as cyclomaltodextrin glucanotrasnferase as disclosed in Japanese Patent Kokai Nos. 139,288/91, 135,992/91 and 183,492/91; or by reacting 5,6-isopropylidene-L-ascorbic acid with β-galactosyl compounds such as lactose in the presence of β-galactosidase as disclosed in Japanese Patent Kokai Nos. 228,183/94 and 263,790/94. Examples of commercially available 2-glucopyranosyl-L-ascorbic acids are "AA 2G", 2-O-α-D-monoglucopyranosyl-L-ascorbic acid with a purity of at least 98%, based on a dry solid basis (d.s.b.), commercialized by Hayashibara Shoji, Inc., Okayama, Japan. Depending on use, the glycosyl-L-ascorbic acids usable in the present invention should not necessarily be highly-purified ones, and can be unseparated ones comprising the glycosyl-L-ascorbic acids, their related compounds, and/or another ingredients formed depending on the preparation methods used, or can be mixtures with another ingredients that do not substantially hinder the acylation.

When employing chemical reactions, methods generally used for acylating compounds with hydroxyl groups can be used, for example, those using acylating agents such as acids, acid halides, acid anhydrides, and acid esters. In general, the acylating agents include carboxylic acids, carboxylic halides, carboxylic acid anhydrides, and carboxylic acid esters, which have carbon atoms of an integer selected generally from 3–20, and preferably from 4–18, and lower and higher fatty acids as base skeletons; propionic acid, butyric acid, isobutyric acid, n-valerianic acid, isovaleric acid, trimethyl acetate, caproic acid, n-heptanoic acid, caprylic acid, pelargonic acid, n-capric acid, lauric acid, myristic acid, palmitic acid, palmitoleic acid, stearic acid, oleic acid, ricinoleic acid, arachidic acid, petroselinic acid, vaccenic acid, linoleic acid, linolenic acid, eleostearic acid, licanic acid, parinaric acid, tariric acid, gadoleic acid, and arachidonic acid.

The acylating reaction is usually conducted in nonaqueous systems free from water invasion to the reaction systems; glycosyl-L-ascorbic acids are reacted either with carboxylic acid anhydride in organic solvents such as pyridine, dimethylsulfoxide, and N,N-dimethylformamide, and if necessary in the presence of catalysts such as p-toluene sulfonic acid; or with carboxylic acid directly in the presence of catalysts such as concentrated sulfuric acid. As for the reaction conditions usable in the present invention, those for acylating L-ascorbic acid in general can be used without modification. When reacting one mole of a glycosyl-L-ascorbic acid with three or fewer moles, or preferably two or fewer moles of an acylating agent, the reaction almost proceeds specifically, resulting in an introduction of an acyl group to a specific position in L-ascorbic acid residue. In the case of 2-O-α-D-monogluco-pyranosyl-L-ascorbic acid, the reaction using two or fewer moles of an acylating agent can acylate substantially only the hydroxyl group at C-6 of L-ascorbic acid. A monoacyl derivative of 2-glucopyranosyl-L-ascorbic acid, wherein only the hydroxyl group at C-6 of L-ascorbic acid is acylated, can be obtained by acylating only the hydroxyl group at C-6 of L-ascorbic acid by conventional methods, and by reacting the acyl L-ascorbic acid with α-glucosyl compounds such as cyclomaltodextrins and partial starch hydrolysates in appropriate organic solvents or appropriate mixtures of organic solvents and water in the presence of, for example, saccharide-transferring enzymes such as cyclomaltodextrin glucanotransferase.

In the case of using enzymatic reactions, glycosyl-L-ascorbic acid and acylating agents are used as substrates. In general, appropriate organic solvents suitable for these substrates and enzymes can be used, or a binary system of water and an organic solvent with an appropriate partition coefficient can be used. Lipase is commonly used as an enzymes, and enzyme preparations can be used in an immobilized form. The organic solvents used in the present invention include readily-water soluble organic solvents such as sec-butyl alcohol, t-butyl alcohol, t-amyl alcohol, dioxane, tetrahydrofuran, diethyl ether, dichloromethane, pyridine, etc. The reaction conditions used in the present invention can be set similarly as in the acylation of L-ascorbic acid using enzymatic reactions, and any type of enzymes can be freely used. Unlike the acylation of L-ascorbic acid, glycosyl-L-ascorbic acids, particularly, 2-glucopyranosyl-L-ascorbic acid needs no complicated reaction conditions for acylation because it is highly stable in aqueous solutions.

Then acyl derivatives can be purified by applying general methods for purifying fatty acid esters of L-ascorbic acid. Examples of respective purification methods are salting out, dialysis, filtration, concentration, separatory sedimentation, separatory extraction, gel chromatography, ion exchange chromatography, high-performance liquid chromatography (HPLC), gas chromatography, affinity chromatography, gel electrophoresis, isoelectrophoresis, crystallization, etc., which are employed in an appropriate combination depending on reaction conditions and the types and purity of the desired acyl derivatives.

The acyl derivatives thus obtained have the following properties:
(1) Compared with L-ascorbic acid and conventional inorganic acid esters, the acyl derivatives have a higher oil-solubility. By controlling the chain length of alkyl groups, an effective water-solubility can be attained while acquiring a satisfactory oil-solubility;
(2) Unlike conventional fatty acid esters and inorganic acid esters, the acyl derivatives release L-ascorbic acid in vivo, resulting in an exertion of the physiological actions inherent to L-ascorbic acid while having a higher safety;
(3) Unlike L-ascorbic acid, the acyl derivatives are highly stable to heat, light, oxygen, and metal ions;
(4) Unlike L-ascorbic acid, the acyl derivatives do not induce a reaction such as the Maillard reaction because they have no direct reducibility;
(5) Unlike L-ascorbic acid and conventional inorganic esters, the acyl derivatives have a higher permeability to skin and mucosas;
(6) Similarly as L-ascorbic acid, the acyl derivatives have a property of entrapping radicals formed in vivo; and
(7) Depending on the types of acylating agents used and the purification level, the acyl derivatives are generally tasteless, odorless, and colorless.

Because of these properties, the present acyl derivatives can be arbitrarily used as stable and safe sources of L-ascorbic acid in the fields of food products, cosmetics, and pharmaceuticals, which need the physiological properties of L-ascorbic acid. The present acyl derivatives can be also used in the fields similarly as above, where the properties of acyl derivatives and/or L-ascorbic acids are needed, for example, they can be used as antioxidants, stabilizers, taste-imparting agents, buffers, emulsification accelerators, and ultraviolet absorbers, as well as reaction materials, reaction intermediates, and reagents used in chemical industries. Among the acyl derivatives, those having a relatively-long chain length of acyl groups, particularly, those having acyl groups having carbon atoms of an integer of at least eight can be most advantageously used in the fields of cosmetics and pharmaceuticals because they have an extremely-high permeability to skin and mucosas.

Explaining in detail their uses in each of the fields, the acyl derivatives according to the present invention can be mixed with, for example, one or more materials and/or ingredients generally used in food products such as water, alcohols, amylaceous substances, proteins, fibers, saccharides, lipids, fatty acids, vitamins, minerals, flavors, colors, sweeteners, seasonings, and antiseptics. The compositions thus obtained can be formed into liquids, suspensions, creams, pastes, jellies, powders, granules, or solids with other desired shapes. Independently of their forms and shapes, all the above food products contain the present acyl derivatives in an amount of at least 0.01 w/w %, and preferably at least 0.1 w/w %.

The food products for which the present invention is arbitrarily applied are, for example, seasonings such as a soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, "chuka-no-moto" (an instant mix for Chinese dish), instant stew mix, instant soup mix "dashi-no-moto" (an instant stock mix), mixed seasoning, "mirin" (a sweet sake), "shin-mirin" (a synthetic mirin), table sugar, and coffee sugar; "wagashi" (Japanese cakes) such as a "senbei" (a rice cracker), "arare" (a rice cake), "okoshi" (a millet-and-rice cake), fried dough cake, "gyuhi" (starch paste), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella, and "amedama" (a Japanese toffee); confectioneries such as a bun, biscuit, cracker, cookie, pie, pudding, cream puff, waffle, sponge cake, doughnut, chocolate, chewing gum, caramel, candy, and gummy jelly; frozen desserts such as an ice cream, ice candy, and sherbet; syrups such as a "korimitsu" (a sugar syrup for shaved ice); spreads and pastes such as a butter cream, custard cream, flour paste, peanut paste, and fruit paste; processed fruits and vegetables such as a jam, marmalade, "syrup-zuke" (a fruit pickle), and "toka" (a conserve); processed cereal foods such as a bun, noodle, cocked rice, and artificial meat; oil and fat foods such as a salad oil and margarine; pickles and pickled products such as a "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and floated-type kamaboko (a Japanese deep-fat fried fish paste); "chinmi" (relishes) such as a "uni-no-shiokara" (salted guts of sea urchin), "ika-no-shiokara" (salted guts of squid), "su-konbu" (a processed tangle), "saki-surume" (dried squid strips), and "fugu-no-mirin-boshi" (a dried mirin-seasoned swellfish); boiled foods such as those cooked with agricultural products, livestocks, and fisheries; daily dishes such as a boiled food, grilled food, fry, fried food, steamed food, and dishes dressed with sauce; frozen foods such as a shrimp for frying, croquette, shu-mai, fried or steamed dumpling stuffed with minced pork, "harumaki" (a kind of Chinese dish), hamburger stake, meat ball, fish hamburger, and fish ball; retort foods such as a hamburger, meat ball, rice boiled together with red beans, rice boiled with beef or chicken, gruel of unpolished rice, curry, meat sauce, demiglace sauce, potage soup, consomme soup, stew, Japanese hotchpotch, "happosai" (a kind of Chinese vegetable), boiled bean, grilled chicken, pot-steamed hotchpotch, boiled chestnut, and vegetable boiled in water; egg and milk products such as a "kinshi-tamago" (a stripped egg roll), milk beverage, butter, and cheese; canned and bottled products such as those of meats, fish meats, fruits, and vegetables; alcohols such as a synthetic sake, sakes, wine, and liquors; soft drinks such as a coffee, cocoa, juice, green tea, tea, Oolong tea, mineral beverage, carbonated beverage, sour milk beverage, and beverage containing lactic acid bacteria; and instant food products such as an instant pudding mix, instant hot cake mix, instant juice, instant coffe, "sokuseki-shiruco" (an instant mix of adzuki-bean soup with rice cake), and instant soup mix. The present acyl derivatives, having a property of entrapping radicals formed in vivo, can be advantageously used in health foods and supplemental health-foods directed for preventing life-style related diseases and geriatric diseases. In addition to foods for humans, the acyl derivatives can be also used in feeds and pet foods for animals such as domestic animals, poultry, honey bees, silk warms, and fishes.

In cosmetic fields, since the present acyl derivatives have a relatively-higher permeability to the skins and mucosas, the derivatives can be arbitrarily used in cosmetics in general including those for the skin, hair, and orally-usable products. The acyl derivatives can be mixed with cosmetically usable ingredients in general such as oily bases, water-soluble bases, flavors, colors, dyes, refrigerants, humectants, emollients, emulsifiers, gelation agents, viscosity enhancers, surfactants, stabilizers for foaming, clearances, antioxidants, adipositas agents, germicides, putrefactive agents, coating-forming agents, and injection agents. The derivatives can be also mixed with one or more medicaments such as vitamins, amino acids, peptides, hormones, extracts, vasodilators, blood circulation-promoting agents, cell-activating agents, anti-inflammatory drugs, urtication-preventing agents, skin-function-promoting agents, and keratolytics. The resulting mixtures can be prepared into products in the form of a liquid, emulsion, cream, paste, powder, granule, or solid of another desired shape. Depending on use, the cosmetics according to the present invention usually contain at least 0.005 w/w %, and preferably at least 0.05 w/w % of the present acyl derivatives.

Examples of the cosmetics for which the present invention can be arbitrarily applied are those for the hair such as hair restorers, hair growth-promoting agents, hair tonics, hair liquids, pomades, chicks, hair lotions, hair creams, hair oils, hair treatments, hair mousses, shampoos, hair rinses, soaps for washing hair; those for the skin such as soaps for washing face, washing powders, creasing creams, body lotions, transparent cosmetic lotions, viscous cosmetic lotions, emulsified cosmetic lotions, vanishing creams, cold creams, nutritive creams, hand creams, powders, foundations, lip sticks, rouges, and packs; those for oral uses such as tooth powders, moisturized dentifrices, toothpastes, tooth washes, medical dentifrices, cachous, and gargles; and another cosmetics such as perfumes, eau de Colongnes, bath salts, underarm deodorants, baby powders, eye lotions, sunburns, and bleaching creams. In the case of cosmetics for the skins and hairs, incorporation of the present acyl derivatives together with about 0.001 w/w % to about 10 w/w % of α-glucosyl bioflavonoids such as α-glucosyl rutin, α-glucosyl hesperidin, and α-glucosyl naringin supplement nutritions to the skins and promote the metabolism in living bodies, resulting in an easy exertion of the effects of the present acyl derivatives. Incorporation of, as humectants, saccharides or sugar alcohols having a moisture-imparting action such as maltose, trehalose, and maltitol in an adequate amount, preferably, not higher than one w/w %, adequately moistens the skins, scalps and/or hairs, and easily exerts the effects of the present acyl derivatives.

In the pharmaceutical field, the present acyl derivatives can be arbitrarily used to treat and/or prevent vitamin-C susceptive diseases including vitamin C-defective diseases, scorbutus, Möller-Barlow disease, ischemic heart disease, and malignant tumors, for example, digestive diseases, circulatory organs' diseases, urinary/genital organs' diseases, cranial nerve diseases, eye diseases, skin diseases, and diseases of the nose, ear and throat. The present acyl derivatives can be used in an effective amount together with the following medicaments used generally in pharmaceuticals, for example, anesthetics, hypnotic analgesics, ataractics, antiepileptics, analgesic-antipyretic/anti-inflammatory drugs, excitations, stimulants, antiparkinsonism drugs, psychoneurosis drugs, central nerve drugs, relaxation drugs skeletal muscles, autonomic nerve drugs, antispastic agents, drugs for eye, drugs for nose and ear, anti-vertiginous drugs, cardiotonics, antiarrhythmic drugs, diuretics, pressure reduction drugs, vasoconstrictors, coronaryvasodilators, peripheral vasodilating drugs, hyperlipemia drugs, breath stimulants, antitussive and expectorant drugs, bronchodilators, drugs for allergy, antidiarrheal drugs, growth drugs, peptic ulcer drugs, stomachic digestants, antacids, cholagogouses, pituitary hormone drugs, salivary gland hormones, thyroid hormone drugs, antithyroid drugs, anabolic steroids, corticosteroids, androgen drugs, estrogen drugs, corpus luteum hormone drugs, mixed hormones, urinary/genital organ drugs, anus drugs, surgical sterilizations/antiseptics, wound protectives, externals for purulent diseases, analgesics, antipruritics, astringents, antiphlogistics, externals for parasite skin diseases, skin-softening drugs, caustics, dental/oral drugs, vitamins, inorganic preparations, supplemental liquids, hemostatics, anticoagulation drugs, drugs for liver diseases, antidotes, habitual intoxication drugs, drugs for treatment of gout, enzyme preparations, diabetic drugs, antioncotics, antihistaminics, drugs for stimulation treatment, antibiotics, chemotherapeutics, biological preparations, anthelmintics, anti-Protozoas, drugs for preparations, X-ray contrast media, and diagnostic drugs. In addition, one or more of adjuvants, excipients, diluents, fillers, stabilizers, antiseptics, colors, and flavors, which ease the intake of the above pharmaceuticals, can be arbitrarily added to the above pharmaceuticals. Depending on use, the resulting compositions can be formed into those in the form of an extract, elixir, capsule, granule; pill, ointment for eye, suspension, emulsion, plaster, suppository, powder, ethanol preparation, tablet, syrup, infusion, decoction, injection, tincture, ophthalmic solution, troche, ointment, cataplasm, aromatic water, liniment, lemonade, fluidextract, lotion, nasal drop, nasal nebula, inhalant for lower airway, sustained release drug for eye, oral mucosal patch, and enema. Depending on use and administration route, the dose of the present acyl derivatives is usually selected from 0.001 to 100 g per adult per day.

The acyl derivatives according to the present invention are incorporated into foods, cosmetics and pharmaceuticals in a prescribed amount before completion of their processings using methods such as mixing, kneading, dissolving, soaking, sprinkling, applying, spraying, and injecting. In the case of having a free carboxyl-group, the acyl derivatives can be subjected to the action of hydroxides of sodium, calcium, magnesium, iron, copper, zinc, and ammonium to form salts of the acyl derivatives.

The following examples describe the preferred embodiments according to the present invention.

EXAMPLE A-1

Butyric Acid Derivative

EXAMPLE A-1(a)

Preparation of Butyric Acid Derivative 2.71 grams (8.0 mmol) of "AA 2G" or 2-glucopyranosyl-L-ascorbic acid, a product containing at least 98% of 2-O-

α-D-monoglucopyranosyl-L-ascorbic acid, d.s.b., commercialized by Hayashibara Shoji, Inc., Okayama, Japan, was placed in a reaction container at ambient temperature, mixed with 350 ml pyridine in a stream of argon gas, and stirred until dissolved. 9.6 mmol of butyric anhyride, dissolved previously in 50 ml pyridine, was dropped away in the reaction container over two minutes, and the mixture was reacted at ambient temperature for 135 min. Thereafter, methanol was added to the reaction mixture, and the resultant was concentrated and dried to suspend the reaction. 4.65 grams of the resulting solid reaction mixture was fed to a column packed with 139.5 g "WAKO GEL", a silica gel for column chromatography, commercialized by Wako Pure Chemicals Industries, Ltd., Tokyo, Japan, and successively eluted with 500 ml ethyl acetate, 500 ml of a solvent system of ethyl acetate and methanol (9:1 by volume), 500 ml of a solvent system of ethyl acetate and methanol (8:2 by volume), 500 ml of a solvent system of ethyl acetate and methanol (7:3 by volume) while collecting 100-ml aliquots of eluates. These fractions were respectively sampled and dropped in a small amount on "SILICA GEL 60 F254", a silica gel plate for thin layer chromatography, commercialized by Merck Research Laboratories, Rahway, USA, followed by drying the plates and then developing the samples with a developer consisting of ethyl acetate and methanol (6:4 by volume). After development, the plate was dried for determining fractions containing a component, which moved on the plate and gave an Rf value of about 0.34 when radiated at a wavelength of 254 nm ultraviolet ray, and then the fractions were pooled, concentrated, and dried.

2.09 grams of the resulting solid was purified again on column chromatography similarly as above, and fractions containing a component, which moved on a plate and gave an Rf value of about 0.34, were pooled, concentrated, and dried to obtain 1.19 g of a tasteless, odorless white fine granule in a yield of 36.4%.

EXAMPLE A-1(b)

Identification of Butyric Acid Derivative

An acyl derivative obtained by the method in Example A-1(a) was measured for mass (m/z) by conventional fast atom bombardment mass spectrometry (abbreviated as "FAB-MS" hereinafter), revealing that the compound gave characteristic peaks at 431 ([M+Na]$^+$) and 409 ([M+H]$^+$).

The acyl derivative was measured in the usual manner for spectra on $^1$H-nuclear magnetic resonance (abbreviated as "$^1$H-NMR") and $^{13}$C-nuclear magnetic resonance (abbreviated as "$^{13}$C-NMR"). Table 1 shows both the chemical shifts of the signals for the spectra, and the assignments of hydrogen- and carbon-atoms. Table 2 shows both the chemical shifts of the signals for the spectra on $^1$H-NMR and $^{13}$C-NMR, and the assignments of hydrogen- and carbon-atoms of 2-O-α-D-monoglucopyranosyl-L-ascorbic acid.

TABLE 1

| Assignment of hydrogen- | Chemical shift in a solvent of CD$_3$OD | |
|---|---|---|
| and carbon-atoms | $^1$H-NMR(δ, J in Hz) | $^{13}$C-NMR(δ) |
| Ascorbic acid residue | | |
| C-1 | — | 174.92 |
| C-2 | — | 120.23 |
| C-3 | — | 162.71 |
| C-4 | 4.80(d, J=1.8 Hz) | 77.44 |

TABLE 1-continued

| Assignment of hydrogen- | Chemical shift in a solvent of CD$_3$OD | |
|---|---|---|
| and carbon-atoms | $^1$H-NMR(δ, J in Hz) | $^{13}$C-NMR(δ) |
| C-5 | 4.13(ddd, J=1.8, 6.1, 7.3 Hz) | 67.97 |
| C-6a | 4.18(dd, J=6.1, 11.0 Hz) | 65.62 |
| C-6b | 4.26(dd, J=7.3, 11.0 Hz) | |
| Glucose residue | | |
| C-1 | 5.36(d, J=3.7 Hz) | 101.74 |
| C-2 | 3..52(dd, J=3.7, 9.7 Hz) | 73.43 |
| C-3 | 3.78(t, J=9.7 Hz) | 74.53 |
| C-4 | 3.40(t, J=9.7 Hz) | 71.20 |
| C-5 | 4.04(ddd, J=2.4 4.9, 9.7 Hz) | 74.81 |
| C-6a | 3.70(dd, J=4.9, 11.9 Hz) | 62.23 |
| C-6b | 3.79(dd, J=2.4, 11.9 Hz) | |
| Butyric acid | | |
| C-1 | — | 172.32 |
| C-2 | 2.35(t, J=7.3 Hz) | 36.77 |
| C-3 | 1.66(sxt, J=7.3 Hz) | 19.35 |
| C-4 | 0.96(t, J=7.3 Hz) | 13.90 |

TABLE 2

| Assignment of hydrogen- | Chemical shift in a solvent of D$_2$O | |
|---|---|---|
| and carbon-atoms | $^1$H-NMR(δ, J in Hz) | $^{13}$C-NMR(δ) |
| Ascorbic acid residue | | |
| C-1 | — | 175.03 |
| C-2 | — | 120.33 |
| C-3 | — | 165.70 |
| C-4 | 5.00(d, J=1.4 Hz) | 79.25 |
| C-5 | 4.10(td, J=1.4, 7.0 Hz) | 71.54 |
| C-6 | 3.75(d, J=7.0 Hz) | 64.73 |
| Glucose residue | | |
| C-1 | 5.57(d, J=3.8 Hz) | 101.60 |
| C-2 | 3.68(dd, J=3.8, 9.8 Hz) | 73.78 |
| C-3 | 3.86(t, J=9.8 Hz) | 75.22 |
| C-4 | 3.51(t, J=9.8 Hz) | 71.67 |
| C-5 | 3.99(dt, J=3.4 9.8 Hz) | 75.74 |
| C-6 | 3.78(d, J=3.4 Hz) | 62.82 |

In Tables 1 and 2, the facts that the chemical shift of the hydrogen, bound to C-6 of L-ascorbic acid, shifted to a lower magnetic field, i.e., from 3.75 to 4.26, before and after the acylation; and that the chemical shift of C-6 of L-ascorbic acid shifted to a lower magnetic field by a large margin, i.e., form 64.73 to 65.62, show that butyric acid residue linked to the hydroxyl group at C-6 of L-ascorbic acid in 2-O-α-D-monoglucopyranosyl-L-ascorbic acid. The acyl derivative was measured for absorption in an acid- and alkaline solutions in the usual manner to give maximum absorption spectra at around wavelengths of 233.8 and 260.2 nm. Similarly as above, the acyl derivative was measured for molecular absorption coefficient to give 9,630 and 14,700 in an acid and alkaline solutions, respectively.

Based on a systematic analysis of the data on spectrochemical analysis and the acylating agents and reaction conditions used in the reaction, the acyl derivative obtained in this example was identified with an acyl derivative in which butyric acid residue linked to the hydroxyl group at C-6 of L-ascorbic acid in 2-O-α-D-monoglucopyranosyl-L-ascorbic acid, i.e., 6-O-butyryl-2-O-α-D-monoglucopyranosyl-L-ascorbic acid (abbreviated as "6-Buty-AA-2G" hereinafter).

EXAMPLE A-2

Preparation of N-caproic Acid Derivative

Using caproic anhydride as an acylating agent, compounds were reacted similarly as in Example A-1(a) except for extending the reaction time to 195 min. After reaction, the reaction product was purified on column chromatography similarly as in Example A-1(a), and fractions containing a component, moved to a position at an Rf value of around 0.36 on thin layer chromatography, were collected, pooled and dried to obtain a tasteless, odorless, white fine granule of acyl derivative in which n-caproic acid residue linked to the hydroxyl group at C-6 of L-ascorbic acid in 2-O-α-D-monoglucopyranosyl-L-ascorbic acid, i.e., 2-O-α-D-monoglucopyranosyl-6-O-hexanoyl-L-ascorbic acid (abbreviated as "6-Hexa-AA-2G", hereinafter) in an amount of 1.51 g and in a yield of 43.2%.

Similar analysis as in Example A-1(b) showed that the acyl derivative in this example gave characteristic peaks at 481 ([(M−H)+2Na]$^+$) and 459 ([M+Na]$^+$) on FAB-MS, and Table 3 showed that the chemical shifts of the signals of the derivative on $^1$H-NMR and $^{13}$C-NMR, and the assignments of hydrogen- and carbon-atoms. The acyl derivative in this example showed the maximum absorption spectra at wavelengths of 233.2 and 260.4 nm, and molecular absorption coefficients of 9,650 and 14,780 in an acid and alkaline solutions, respectively.

TABLE 3

| Assignment of hydrogen- and carbon-atoms | Chemical shift in a solvent of CD$_3$OD | |
|---|---|---|
| | $^1$H-NMR(δ, J in Hz) | $^{13}$C-NMR(δ) |
| Ascorbic acid residue | | |
| C-1 | — | 175.11 |
| C-2 | — | 120.17 |
| C-3 | — | 163.11 |
| C-4 | 4.79(s) | 77.50 |
| C-5 | 4.13(dd, J=6.1, 7.3 Hz)Hz) | 68.00 |
| C-6a | 4.18(dd, J=6.1, 10.8 Hz) | 65.65 |
| C-6b | 4.26(dd, J=7.3, 10.8 Hz) | |
| Glucose residue | | |
| C-1 | 5.36(d, J=3.7 Hz) | 101.77 |
| C-2 | 3.52(dd, J=3.7, 9.7 Hz) | 73.46 |
| C-3 | 3.78(t, J=9.7 Hz) | 74.54 |
| C-4 | 3.39(t, J=9.7 Hz) | 71.24 |
| C-5 | 4.04(ddd, J=2.4, 4.9, 9.7 Hz) | 74.80 |
| C-6a | 3.70(dd, J=4.9, 11.7 Hz) | 62.26 |
| C-6b | 3.80(dd, J=2.4, 11.7 Hz) | |
| n-Caproic acid | | |
| C-1 | — | 172.46 |
| C-2 | 2.37(t, J=7.3 Hz) | 34.84 |
| C-3 | 1.63(qn, J=7.3 Hz) | 25.64 |
| C-4 & 5 | 1.34(m) | 23.33, 32.37 |
| C-6 | 0.92(t, j=7.3 Hz) | 14.21 |

EXAMPLE A-3

Preparation of Caprylic Acid Derivative

Using caprylic anhydride as an acylating agent, compounds were reacted similarly as in Example A-1(a) except for extending the reaction time to 165 min. After reaction, the reaction product was purified on column chromatography similarly as in Example A-1(a), and fractions containing a component, moved to a position at an Rf value of around 0.40 on thin layer chromatography, were collected, pooled and dried to obtain a tasteless, odorless, white fine granule of acyl derivative in which caprylic acid residue linked to the hydroxyl group at C-6 of L-ascorbic acid in 2-O-α-D-monoglucopyranosyl-L-ascorbic acid, i.e., 2-O-α-D-monoglucopyranosyl-6-O-octanoyl-L-ascorbic acid (abbreviated as "6-Octa-AA-2G", hereinafter) in an amount of 1.35 g and in a yield of 36.3%.

Similar analysis as in Example A-1(b) showed that the acyl derivative in this example gave characteristic peaks at 509 ([(M−H)+2Na]$^+$) and 459 ([M+Na]$^+$) on FAB-MS, and Table 4 showed the chemical shifts of the signals of the compound on $^1$H-NMR and $^{13}$C-NMR, and the assignments of hydrogen- and carbon-atoms. The acyl derivative in this example showed the maximum absorption spectra at wavelengths of 233.2 and 260.6 nm, and molecular absorption coefficients of 9,610 and 14,430 in an acid and alkaline solutions, respectively.

TABLE 4

| Assignment of hydrogen- and carbon-atoms | Chemical shift in a solvent of CD$_3$OD | |
|---|---|---|
| | $^1$H-NMR(δ, J in Hz) | $^{13}$C-NMR(δ) |
| Ascorbic acid residue | | |
| C-1 | — | 175.08 |
| C-2 | — | 120.21 |
| C-3 | — | 162.92 |
| C-4 | 4.80(s) | 77.47 |
| C-5 | 4.13(dd, J=6.1, 7.3 Hz)Hz) | 67.97 |
| C-6a | 4.18(dd, J=6.1, 11.0 Hz) | 65.62 |
| C-6b | 4.26(dd, J=7.3, 11.0 Hz) | |
| Glucose residue | | |
| C-1 | 5.36(d, J=3.7 Hz) | 101.77 |
| C-2 | 3.52(dd, J=3.7, 9.6 Hz) | 73.44 |
| C-3 | 3.78(t, J=9.6 Hz) | 74.53 |
| C-4 | 3.39(t, J=9.6 Hz) | 71.23 |
| C-5 | 4.04(ddd, J=2.4, 4.9, 9.6 Hz) | 74.80 |
| C-6 a | 3.70(dd, J=4.9, 11.6 Hz) | 62.25 |
| C-6 b | 3.80(dd, J=2.4, 11.6 Hz) | |
| Caprylic acid | | |
| C-1 | — | 172.39 |
| C-2 | 2.37(t, J=7.3 Hz) | 34.88 |
| C-3 | 1.63(qn, J=7.3 Hz) | 25.95 |
| C-4 to 7 | 1.32(m) | 23.61, 30.02, 30.12, 32.81 |
| C-8 | 0.90(t, J=7.3 Hz) | 14.36 |

EXAMPLE A-4

Preparation of N-capric Acid Derivative

Using n-capric anhydride as an acylating agent, compounds were reacted similarly as in Example A-1(a) except for extending the reaction time to 195 min. After reaction, the reaction product was purified on column chromatography similarly as in Example A-1(a), and fractions containing a component, moved to a position at an Rf value of around 0.40 on thin layer chromatography, were collected, pooled and dried to obtain a tasteless, odorless, white fine granule of acyl derivative in which n-capric acid residue linked to the hydroxyl group at C-6 of L-ascorbic acid in 2-O-α-D-monoglucopyranosyl-L-ascorbic acid, i.e., 6-O-decanoyl-2-O-α-D-monoglucopyranosyl-L-ascorbic acid (abbreviated as "6-Deca-AA-2G", hereinafter) in an amount of 0.55 g and in a yield of 13.9%.

Similar analysis as in Example A-1(b) showed that the acyl derivative in this example gave characteristic peaks at 537 ([(M−H)+2Na]$^+$) and 515 ([M+Na]$^+$) on FAB-MS, and Table 5 showed the chemical shifts of the signals of the derivative on $^1$H-NMR and $^{13}$C-NMR, and the assignments of hydrogen- and carbon-atoms. The acyl derivative in this example showed the maximum absorption spectra at wavelengths of 233.6 and 259.8 nm, and molecular absorption coefficients of 9,880 and 14,870 in an acid and alkaline solutions, respectively.

TABLE 5

| Assignment of hydrogen- and carbon-atoms | Chemical shift in a solvent of CD$_3$OD | |
|---|---|---|
| | $^1$H-NMR($\delta$, J in Hz) | $^{13}$C-NMR($\delta$) |
| Ascorbic acid residue | | |
| C-1 | — | 175.11 |
| C-2 | — | 120.17 |
| C-3 | — | 163.46 |
| C-4 | 4.78(d, J=1.2 Hz) | 77.55 |
| C-5 | 4.13(ddd, J=1.2, 6.1, 6.7 Hz) | 68.02 |
| C-6a | 4.18(dd, J=6.1, 11.0 Hz) | 65.65 |
| C-6b | 4.25(dd, J=6.7, 11.0 Hz) | |
| Glucose residue | | |
| C-1 | 5.35(d, J=3.7 Hz) | 101.79 |
| C-2 | 3.51(dd, J=3.7, 9.6 Hz) | 73.46 |
| C-3 | 3.77(t, J=9.6 Hz) | 74.55 |
| C-4 | 3.39(t, J=9.6 Hz) | 71.27 |
| C-5 | 4.04(ddd, J=2.4 4.9, 9.6 Hz) | 74.79 |
| C-6a | 3.70(dd, J=4.9, 11.6 Hz) | 62.28 |
| C-6b | 3.80(dd, J=2.4, 11.6 Hz) | |
| n-Capric acid | | |
| C-1 | — | 172.58 |
| C-2 | 2.37(t, J=7.3 Hz) | 34.88 |
| C-3 | 1.62(qn, J=7.3 Hz) | 25.96 |
| C-4 to 9 | 1.30(m) | 23.67, 30.16, 30.35(2xC) 30.52, 32.99 |
| C-10 | 0.90(t, J=6.7 Hz) | 14.39 |

EXAMPLE A-5

Preparation of Lauric Acid Derivative

Using lauric anhydride as an acylating agent, compounds were reacted similarly as in Example A-1(a) except for extending the reaction time to 165 min. After reaction, the reaction product was purified on column chromatography similarly as in Example A-1(a), and fractions containing a component, moved to a position at an Rf value of around 0.42 on thin layer chromatography, were collected, pooled and dried to obtain a tasteless, odorless, white fine granule of acyl derivative in which lauric acid residue linked to the hydroxyl group at C-6 of L-ascorbic acid in 2-O-α-D-monoglucopyranosyl-L-ascorbic acid, i.e., 6-O-dodecanoyl-2-O-α-D-monoglucopyranosyl-L-ascorbic acid (abbreviated as "6-Dode-AA-2G", hereinafter) in an amount of 1.93 g and in a yield of 46.4%.

Similar analysis as in Example A-1(b) showed that the acyl derivative in this example gave characteristic peaks at 565 ([(M–H)+2Na]$^+$) and 543 ([M+Na]$^+$) on FAB-MS, and Table 6 showed the chemical shifts of the signals of the compound on $^1$H-NMR and $^{13}$C-NMR, and the assignments of hydrogen- and carbon-atoms. The acyl derivative in this example showed the maximum absorption spectra at wavelengths of 233.2 and 260.2 nm, and showed molecular absorption coefficients of 9,820 and 14,680 in an acid and alkaline solutions, respectively.

TABLE 6

| Assignment of hydrogen- and carbon-atoms | Chemical shift in a solvent of CD$_3$OD | |
|---|---|---|
| | $^1$H-NMR($\delta$, J in Hz) | $^{13}$C-NMR($\delta$) |
| Ascorbic acid residue | | |
| C-1 | — | 175.11 |
| C-2 | — | 119.81 |
| C-3 | — | 165.05 |
| C-4 | 4.74(s) | 77.76 |
| C-5 | 4.13(ddd, J=6.1, 6.7 Hz) | 68.11 |
| C-6a | 4.18(dd, J=6.1, 11.0 Hz) | 65.68 |
| C-6b | 4.25(dd, J=6.7, 11.0 Hz) | |
| Glucose residue | | |
| C-1 | 5.34(d, J=3.7 Hz) | 101.85 |
| C-2 | 3.50(dd, J=3.7, 9.7 Hz) | 73.49 |
| C-3 | 3.78(t, J=9.7 Hz) | 74.58 |
| C-4 | 3.38(t, J=9.7 Hz) | 71.36 |
| C-5 | 4.06(m) | 74.72 |
| C-6a | 3.69(dd, J=4.9, 11.6 Hz) | 62.35 |
| C-6b | 3.81(dd, J=2.4, 11.6 Hz) | |
| Lauric acid | | |
| C-1 | — | 173.09 |
| C-2 | 2.37(t, J=7.3 Hz) | 34.89 |
| C-3 | 1.62(qn, J=7.3 Hz) | 25.95 |
| C-4 to 11 | 1.29(m) | 23.68, 30.16, 30.35, 30.55 30.68(2xC) 33.02 |
| C-12 | 0.90(t, J=6.7 Hz) | 14.40 |

EXAMPLE A-6

Preparation of N-capric Acid Derivative

It was reacted similarly as in Example A-4 except for using as glycosyl-L-ascorbic acid an impurity containing 2-O-α-D-monoglucopyranosyl-L-ascorbic acid, 2-O-α-D-diglucopyranosyl-L-ascorbic acid, 2-O-α-D-triglucopyranosyl-L-ascorbicacid, 2-O-α-D-tetraglucopyranosyl-L-ascorbic acid, 2-O-α-D-pentaglucopyranosyl-L-ascorbic acid, and 2-O-α-D-hexaglucopyranosyl-L-ascorbic acid, which were prepared by the method in Japanese Patent Kokai No. 139,288/91. Thereafter, the reaction products were purified on column chromatography similarly as in Example A-1(a), and fractions containing components, moved to positions at Rf values from about 0.30 to about 0.40 on thin layer chromatography, were collected, pooled and dried to obtain a tasteless, odorless, white powdery composition of acyl derivatives in which n-capric acid residue linked to the hydroxyl group at C-6 of L-ascorbic acid in 2-glucopyranosyl-L-ascorbic acids, i.e., a mixture containing 6-O-dodecanoyl-2-glucopyranosyl-L-ascorbic acids in an amount of 1.25 g.

EXAMPLE A-7

Preparation of Stearic Acid Derivative

It was reacted similarly as in Example A-1 except for using as glycosyl-L-ascorbic acid an impurity containing unseparated compositions similarly as in Example A-6. Thereafter, the reaction products were purified on column chromatography similarly as in Example A-1(a), and fractions containing components, moved to positions at Rf values from about 0.5 to about 0.6 on thin layer chromatography, were collected, pooled and dried to obtain a tasteless, odorless, white powdery composition of acyl derivatives in which stearic acid residue linked to the hydroxyl group at C-6 of L-ascorbic acid in 2-glucopyranosyl-L-ascorbic acids, i.e., 2-gluco-pyranosyl-6-O-stearyl-L-ascorbic acids in an amount of 0.72 g.

The following disclose the solubility, stability, radical-entrapping ability, dynamics, skin-permeability, and anti-scorbutic tests on the acyl derivatives obtained by the methods in Examples A-1 to A-5.

EXPERIMENT 1

Solubility Test

The acyl derivatives, obtained by the methods in Examples A-1 to A-7, were tested for solubility in solvents at ambient temperature. As a result, 6-Buty-AA-2G and 6-Hexa-AA-2G easily dissolved in water, but not 6-Octa-AA-2G, 6-Deca-AA-2G, and 6-Dode-AA-2G. Every acyl derivative easily dissolved in methanol, dissolved in ethanol, hardly dissolved in acetone, and did not dissolve in ethyl acetate and diethyl ether. The unseparated composition of acyl derivative, obtained by the method in Example A-7, dissolved in acetone, but hardly dissolved in ethyl acetate.

L-Ascorbic acid and 2-O-α-D-monoglucopyranosyl-L-ascorbic acid were substantially or completely insoluble in methanol and ethanol, and insoluble in acetone. Thus, the acyl derivatives in Examples A-1 to A-7 have a strongly-higher oil-solubility than L-ascorbic acid and 2-O-α-D-monogluco-pyranosyl-L-ascorbic acid.

EXPERIMENT 2

Stability of Acyl Derivative

One hundred $\mu$mol of any one of acyl derivatives, obtained by the methods in Examples A-1 to A-5, was placed in a 10-ml test tube equipped with a screw cap, mixed with and dissolved in 200 $\mu$l dimethylsulfoxide. To the solution was added 9.8 ml of 100 mM phosphate buffered aqueous solution (pH 7.0), and the aqueous solution was sterilized, and then incubated at 37° C. or 60° C. while the aqueous solution was sampled at prescribed times, followed by freezing the samples instantly at −30° C. for storing. Thereafter, the aqueous solution stored by freezing was thawed, analyzed on HPLC, and determined for the remaining content of the acyl derivatives based on the absorbance at a wavelength of 254 nm. In parallel, a system as a control using L-ascorbic acid or 2-O-α-D-monoglucopyranosyl-L-ascorbic acid in place of the acyl derivatives was provided, treated similarly as in the case of the acyl derivatives, and determined for the remaining content of the L-ascorbic acid or 2-O-α-D-monoglucopyranosyl-L-ascorbic acid. The results of stability tests at 60° C. and 37° C. are respectively presented in FIGS. 1 and 2.

Figure 2:
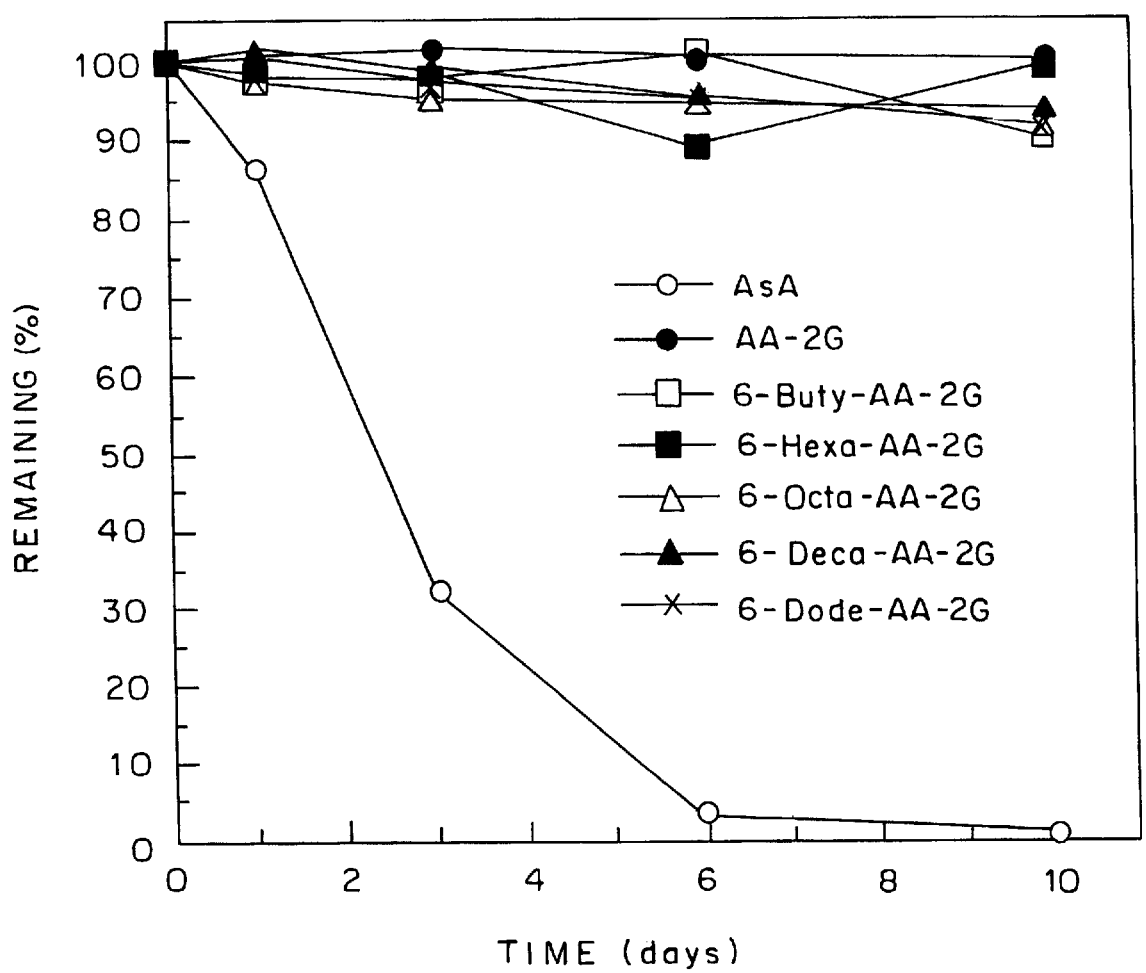
FIG. 2 is a figure that shows the stability of L-ascorbic acid, 2-O-α-D-monoglucopyranosyl-L-ascorbic acid, and the present acyl derivatives in an aqueous solution at 37° C.

As evident from FIGS. 1 and 2, 75.9% activity of L-ascorbic acid was lost when incubated at 60° C. for 12 hours, and 68.3% activity thereof was lost even at 37° C. when incubated for three days. In contrast, independently of the acyl chain length, the acyl derivatives according to the present invention only lost about 15% to about 20% of its activity even when incubated at 60° C. for 48 hours, and only lost about 10% or less of its activity at 37° C. when incubated for 10 days. While 2-O-α-D-monoglucopyranosyl-L-ascorbic acid lost its 3.9% activity when incubated at 60° C. for 48 hours, and lost its 1.6% activity even at 37° C. when incubated for 14 days. These results show that the present acyl derivatives have a higher stability than L-ascorbic acid and have substantially the same stability as 2-O-α-D-monoglucopyranosyl-L-ascorbic acid.

EXPERIMENT 3

Radical-Entrapping Ability 1,1-Diphenyl-2-picrylhydrazyl (hereinafter abbreviated as "DPPH") was dissolved in ethanol to give a concentration of 0.5 mM, and, as test samples, acyl derivatives obtained by the methods in Examples A-1 to A-5 were respectively dissolved in four milliliters of a 50 v/v % aqueous ethanol solution to give a concentration of $1.25 \times 10^{-4}$M, $1.25 \times 10^{-5}$M or $1.25 \times 10^{-6}$M. To each of the test samples placed in containers was added one milliliter of the DPPH ethanol solution, and the containers were filled with argon gas, allowed to stand at ambient temperature for 20 min, and instantly determined for absorbance at a wavelength of 516 nm by a spectrophotometry. In parallel, as a control, a system using a 60 v/v % aqueous ethanol solution was provided in place of the test samples, and treated similarly as in the case of the acyl derivatives. The percentage (%) of the absorbance of the test samples to that of the control was regarded as an oxidation-inhibitory activity, and the activity was used as an index of radical-entrapping ability. The 50% oxidation-inhibitory-concentration ($EC_{50}$) was calculated based on a logarithmic value of a concentration of the test sample used and on an oxidation-inhibitory ability shown by the sample at the concentration. The results are in Table 7.

TABLE 7

| Sample*a | Oxidation inhibitory effect(%)*b | $EC_{50}(\times 10^{-5}M)$ |
| --- | --- | --- |
| AsA | 93.7 | 4.64 |
| AA 2G | 55.4 | 9.03 |
| Butyric acid derivative | 50.1 | 9.98 |
| n-Caproic acid derivative | 55.1 | 9.10 |
| Caprylic acid derivative | 60.4 | 8.27 |
| n-Capric acid derivative | 67.5 | 7.30 |
| Lauric acid derivative | 78.3 | 6.32 |

Note)
*a: AsA and AA 2G represent L-ascorbic acid and 2-O-α-D-monoglucopyranosyl-L-ascorbic acid, respectively.
*b: It shows a value at a concentration of $10^{-4}$M of a sample.

As evident from the results in Table 7, the 5-types of acyl derivatives tested showed a slightly-lower radical-entrapping ability than that of L-ascorbic acid, but they showed a higher radical-entrapping ability than 2-O-α-D-monogluco-pyranosyl-L-ascorbic acid. The results in Table 7 also show the fact that the radical-entrapping ability of the present acyl derivatives increases positively in relation to the acyl chain length. Needless to say, L-ascorbic acids released from the present acyl derivatives exert the same radical-entrapping ability as that of natural L-ascorbic acid.

EXPERIMENT 4

Dynamic Test

Figure 3:
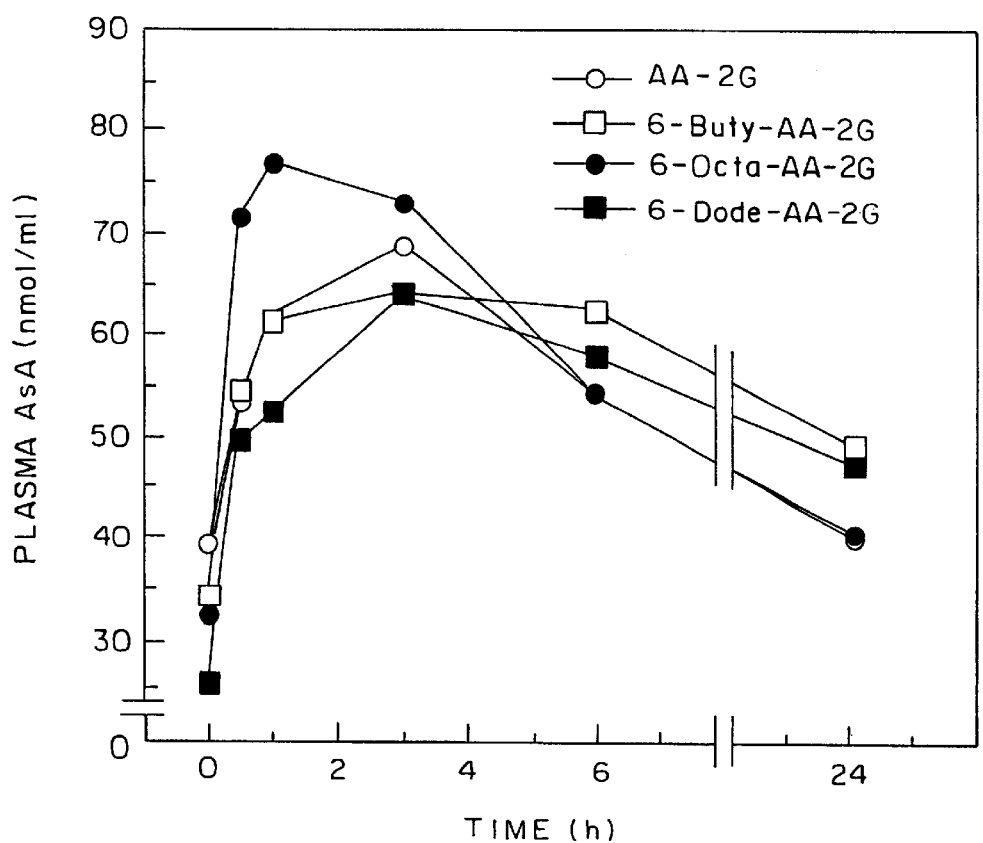
FIG. 3 is a figure that shows the time course of the blood level of L-ascorbic acid in rats administered with 2-O-α-D-monoglucopyranosyl-L-ascorbic acid, and the present acyl derivatives.

Male Wister/ST rats, 12–14-week-old, were fasted for 16 hours and, under an anesthetic, 200-$\mu$l blood was taken from their hearts using a syringe injected with a physiological saline containing 600 units/ml heparin. Just after the taking, either of 2-O-α-D-monoglucopyranosyl-L-ascorbic acid and the acyl derivatives obtained by the methods in Examples A-1 to A-5, which had been dissolved in 500 $\mu$l of superpure water, was orally administered to the rats in an amount corresponding to 56.8 μmol/head of L-ascorbic acid. Just after the administration and after a prescribed period of time from the administration, blood was taken from the rats similarly as above at a prescribed time interval, and the blood taken was admixed with an adequate amount of heparin and instantly centrifuged at 4° C. to collect supernatants. Thereafter, 90 μl of each supernatant was mixed with 5-time-volumes of 450 μl of a 1.06 w/v % metaphosphoric acid aqueous solution, and the mixture was centrifuged at 4° C. for 10 min, followed by collecting 450 μl of a newly formed supernatant and subjecting the supernatant to HPLC to determine the blood level of the acyl derivatives, 2-O-α-D-monoglucopyranosyl-L-ascorbic acid, and L-ascorbic acid. FIG. 3 shows the data partially.

As shown in FIG. 3, when administered orally, the present acyl derivatives instantly increased the blood level of L-ascorbic acid in rats just after the administration to show the maximum level one hour after the administration and exhibit an about 50% of the maximum level even 24 hours after the administration. The administration of the 6-Octa-AA-2G in Example A-3 remarkably increased the blood level of L-ascorbic acid to a level as high as about 1.5 times of that of 2-O-α-D-monoglucopyranosyl-L-ascorbic acid at their peaks. No acyl derivative and 2-O-α-D-monoglucopyranosyl-L-ascorbic acid were detected in the blood of rats when administered with either of the acyl derivatives. These results indicate the present acyl derivatives were absorbed by the digestive tracts to promptly release L-ascorbic acid.

Figure 4:
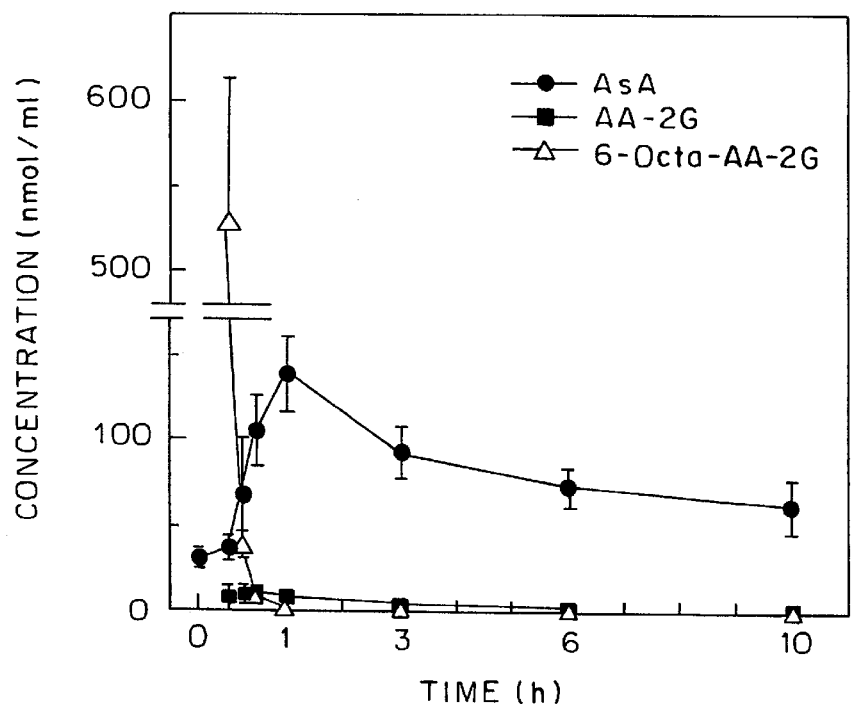
FIG. 4 is a figure that shows the dynamics in the blood level of the present 6-Octa-AA-2G in rats administered with the compound intravenously, and the change of the metabolized products of the compound.

For 6-Octa-AA-2G that showed the maximum level of L-ascorbic acid in the oral administration test, it was tested for dynamics on intravenous administration in accordance with the above oral administration test. In parallel, as for comparison, L-ascorbic acid and 2-O-α-D-monoglucopyranosyl-L-ascorbic acid were tested similarly. FIG. 4 shows the change of the dynamics and the metabolized products when intravenously administered with 6-Octa-AA-2G, and FIG. 5 shows the time course of the blood level of L-ascorbic acid when intravenously administered with 6-Octa-AA-2G, 2-O-α-D-monoglucopyranosyl-L-ascorbic acid, and L-ascorbic acid.

As evident from FIG. 4, the blood level of 6-Octa-AA-2G reached to 524.7 nmol/ml two minutes after the intravenous administration, and then intermittently lowered to a level of 38.2 nmol/ml 15 min after the administration. The blood level of L-ascorbic acid, released from 6-Octa-AA-2G, showed the maximum level one hour after the administration, and even at 10 hours after the administration the blood level was kept at around 50% of the maximum level. The blood level of 2-O-α-D-monoglucopyranosyl-L-ascorbic acid, when administered with 6-Octa-AA-2G, reached to the maximum level of 9.55 nmol/ml within one hour after the administration, and then lowered to an undetectable level.

Figure 5:
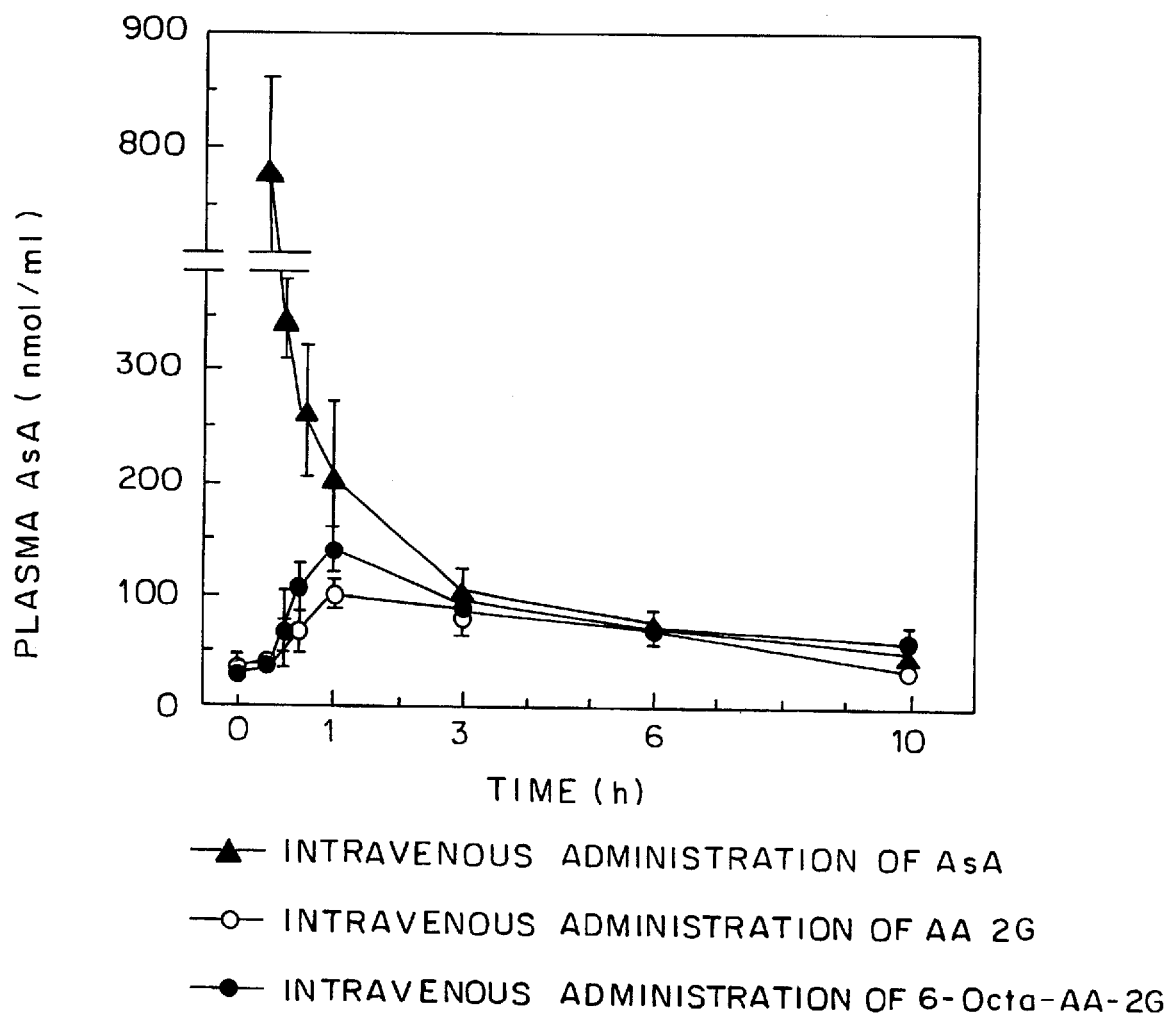
FIG. 5 is a figure that shows the time course in the blood level of L-ascorbic acid, 2-O-α-D-monoglucopyranosyl-L-ascorbic acid, and the present 6-Octa-AA-2G in rats administered with the compounds intravenously.

As shown in FIG. 5, when administered intravenously, 6-Octa-AA-2G exceeded 2-O-α-D-monoglucopyranosyl-L-ascorbic acid with respect to the blood level of L-ascorbic acid throughout this experiment. This indicates that the present acyl derivatives increase the blood level of L-ascorbic acid in a relatively-short period of time when administered intravenously.

EXPERIMENT 5

Skin Permeation Test

For acyl derivatives obtained by the methods in Examples A-1 to A-5, skin-permeability test was conducted using "TESTSKIN", a commercialized human-skin-restructuring-model, produced by Toyobo Co., Ltd., Tokyo, Japan. According to the specification affixed to the product, a medium for assay was injected to a plate for assay in a volume of 1.2 ml/well, and a transferring well, attached with an artificial skin, was loaded on the bottom of the plate, and attached with an assay ring applied with a silicone grease in the middle of the transferring well. Into the assay ring, either of L-ascorbic acid, 2-O-α-D-monoglucopyranosyl-L-ascorbic acid, and acyl derivatives obtained by the methods in Examples A-1 to A-5, which had been dissolved in a medium for assay to give a concentration of 10 mM, followed by incubation at 37° C. for 120 hours while sampling the assay medium in the assay plate at prescribed times, and quantifying the content of the L-ascorbic acid, 2-O-α-D-monoglucopyranosyl-L-ascorbic acid (AA 2G), and acyl derivatives, as well as the total content of L-ascorbic acid. The total content of L-ascorbic acid was determined by adding to the sampled assay medium the same volume of one mole phosphate buffer (pH 7.0), containing one w/v % dithiothreitol, and the same volume of 0.612-N sodium hydroxide, incubating the resulting solution at 45° C. for 30 min to reduce dehydroascorbic acid, and quantifying L-ascorbic acid (AsA) by HPLC.

Figure 6:
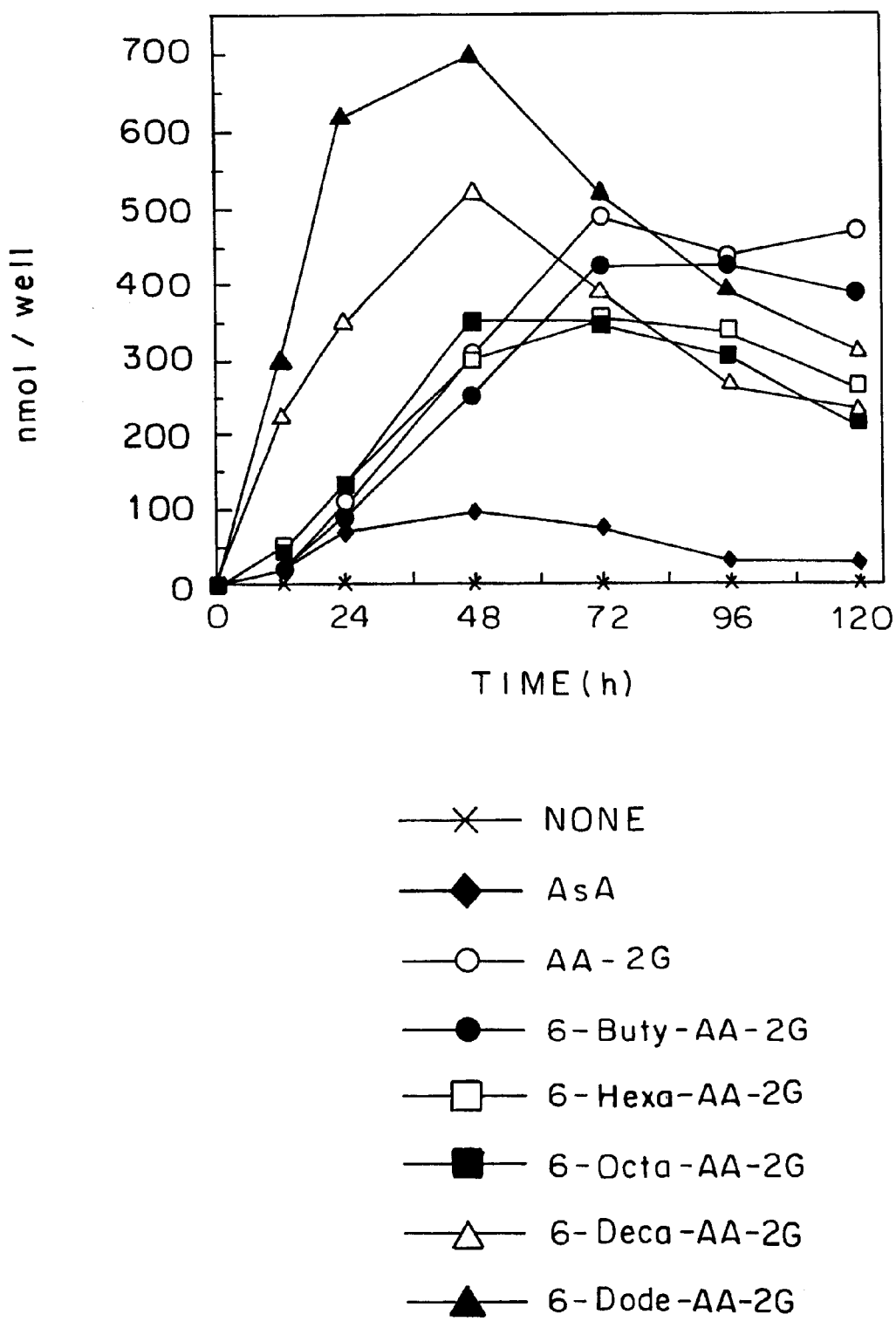
FIG. 6 is a figure that shows the time course of the dynamics of L-ascorbic acid, 2-O-α-D-monoglucopyranosyl-L-ascorbic acid, the present acyl derivatives when permeating into an artificial skin.
Figure 7:
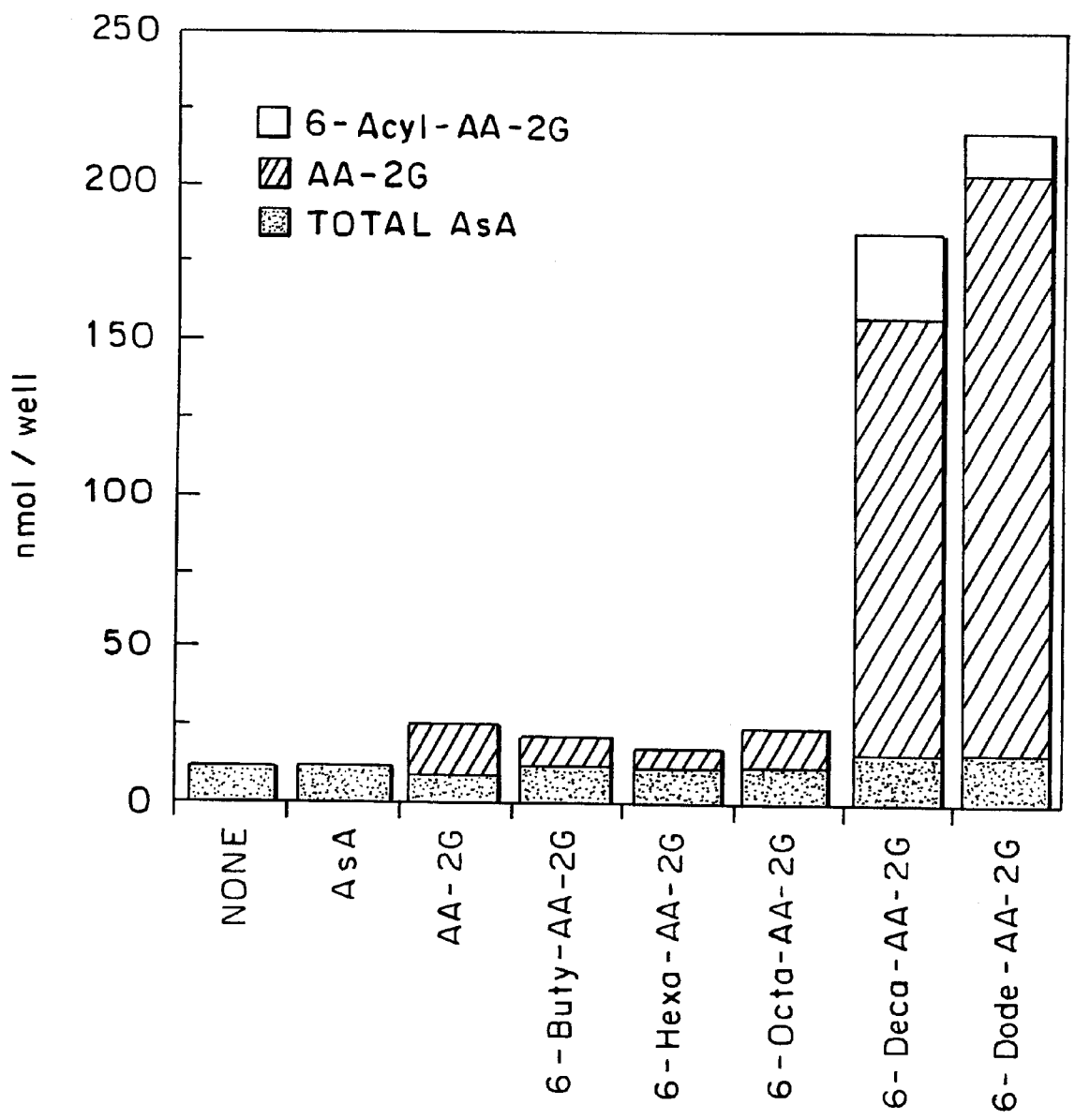
FIG. 7 is a figure that shows the dynamics of the release of L-ascorbic acid and 2-O-α-D-monoglucopyranosyl-L-ascorbic acid when permeating into an artificial skin.
Figure 8:
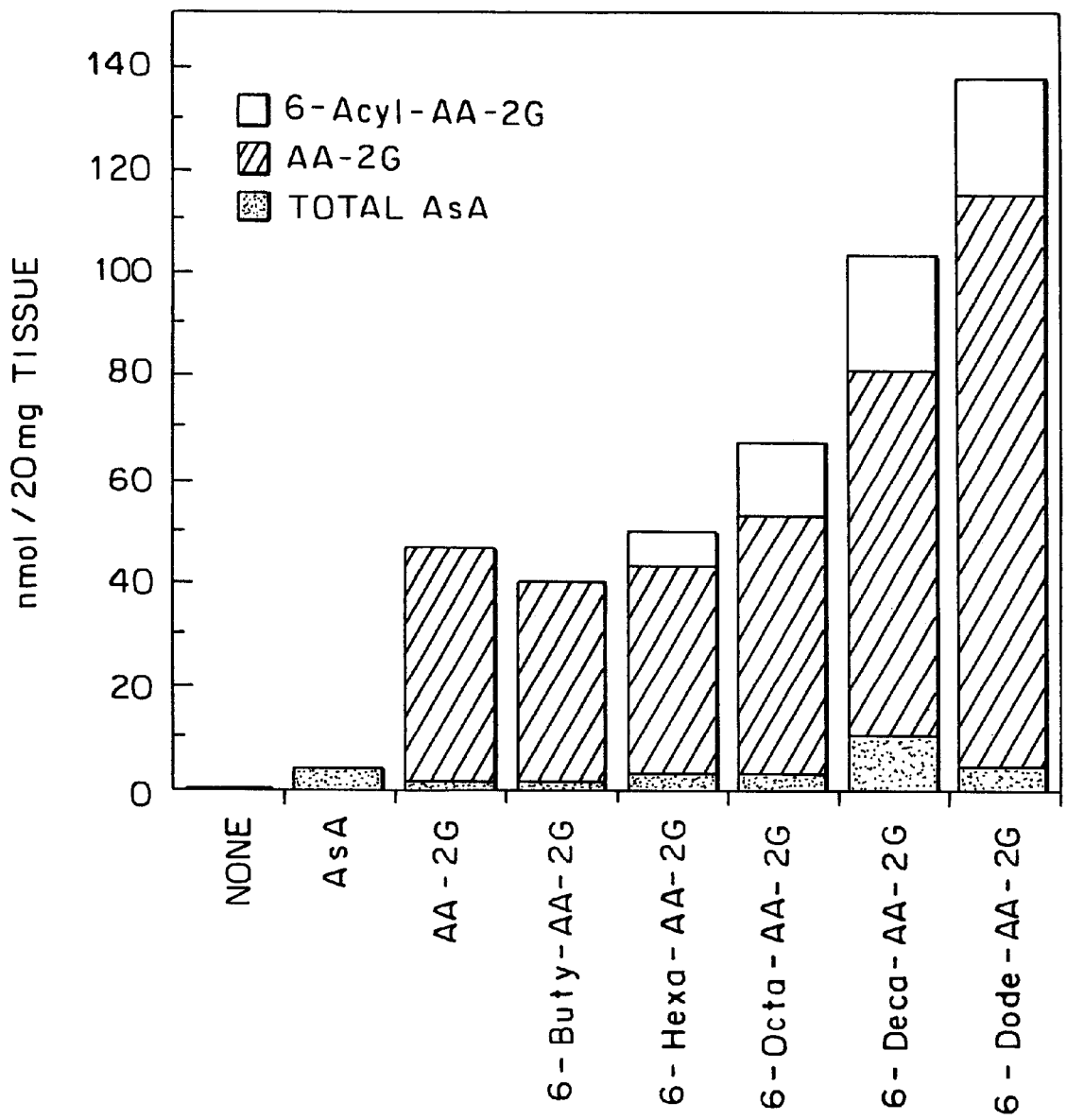
FIG. 8 is a figure that shows the dynamics of L-ascorbic acid, 2-O-α-D-monoglucopyranosyl-L-ascorbic acid, and the present acyl derivatives when releasing L-ascorbic acid and 2-O-α-D-monoglucopyranosyl-L-ascorbic acid within an artificial skin.

After 12-hour incubation, some of the transferring wells were removed, and the center part of the artificial skin in the wells was punched in a diameter of eight millimeters, followed by quantifying L-ascorbic acid, 2-O-α-D-monogluco-pyranosyl-L-ascorbic acid, and acyl derivatives, as well as determining the total content of L-ascorbic acid. The content of the total L-ascorbic acid in the artificial skin was determined by soaking the artificial skin in a 10 w/v % aqueous trichloroacetic acid solution, and ultrasonicated for five minutes, followed by quantifying L-ascorbic acid in the resulting extract similarly as in the case of the assay medium. FIGS. 6, 7 and 8 show a dynamic where L-ascorbic acid, 2-O-α-D-monoglucopyranosyl-L-ascorbic acid, and the present acyl derivatives permeate into the artificial skin; a dynamic where 2-O-α-D-monoglucopyranosyl-L-ascorbic acid and the present acyl derivatives permeate into the artificial skin to release L-ascorbic acid, and the 2-O-α-D-monoglucopyranosyl-L-ascorbic acid; and a dynamic where 2-O-α-D-monoglucopyranosyl-L-ascorbic acid and the present acyl derivatives release L-ascorbic acid and the 2-O-α-D-monoglucopyranosyl-L-ascorbic acid within the artificial skin.

The result in FIG. 6 shows that the acyl derivatives, obtained by the methods in Examples A-1 to A-5, exceed L-ascorbic acid in the skin permeability 3-times or higher than L-ascorbic acid with respect to their peak levels. In particular, the 6-Dode-AA-2G in Example A-5 was particularly superior in the skin permeability, i.e., the peak level was as high as 7-times of that of L-ascorbic acid. The results in FIGS. 7 and 8 indicate that the present acyl derivatives easily release L-ascorbic acid when permeating into the skin. Among the acyl derivatives tested, 6-Deca-AA-2G and 6-Dode-AA-2G were excellent with respect to the skin permeability of L-ascorbic acid; the permeation level reached to a level about 3-times higher than that of L-ascorbic acid.

EXPERIMENT 6

Anti-scorbutus Test

For the acyl derivatives obtained by the methods in Examples A-1 to A-5, they were tested whether they release L-ascorbic acid in vivo, and then exert the physiological action inherent to L-ascorbic acid based on an index for anti-scorbutus action by L-ascorbic acid as a representative physiological action of the compound.

In accordance with the method as reported in *Journal of Pharmacobio-Dynamics*, Vol. 13, pp. 688–695 (1990) by the present inventors, male Hurtley's guinea pigs, 4-week-old, were bred under free intake of water and vitamin C-defective food, commercialized by Oriental Yeast Co., Ltd., Tokyo, Japan, while the guinea pigs were weighed every morning at a prescribed time as an index of the symptom of anti-scorbutus disease. On six days after a significant body-weight-lowering was observed, the guinea pigs were divided into three groups consisting of four heads per group, weighed every morning at a prescribed time, and orally administered, once every morning throughout this experiment, with a specimen of 56.80 µmol/head/shot of either of 2-O-α-D-monoglucopyranosyl-L-ascorbic acid and the present acyl derivatives, obtained by the methods in Examples A-1 to A-5, which had been dissolved in 500 µl superpure water. In parallel, one group as a control, in which guinea pigs were administered with only a fresh preparation of the same water free of the specimens, was provided and treated similarly as in the groups with the specimens.

Figure 9:
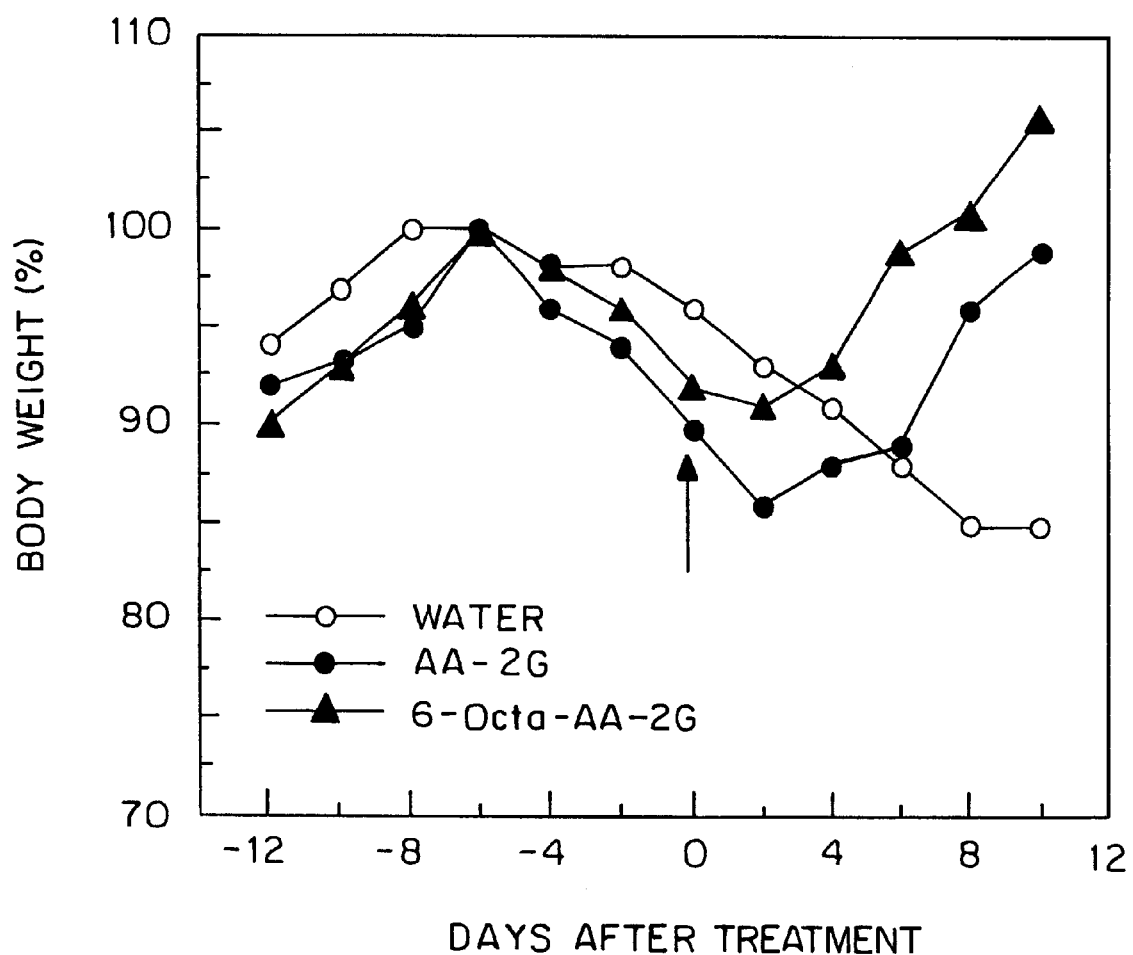
FIG. 9 is a figure that shows the change in the body weight of guinea pigs with scorbutus when administered with water, 2-O-α-D-monoglucopyranosyl-L-ascorbic acid, and 6-Octa-AA-2G.

On six days after the administration of the specimens, the guinea pigs were anatomized according to the method disclosed in the above literature, and were extracted their livers, followed by determining the level of L-ascorbic acid in the liver tissues, observing the occurrence of internal bleeding in joints, etc., and collecting blood from the guinea pigs to determine the blood level of L-ascorbic acid and alkaline phosphatase using plasmas prepared from the collected blood. FIG. 9 shows the body weight change of the guinea pigs before and after the administration of water, 2-O-α-D-monogluco-pyranosyl-L-ascorbic acid, and some of the present acyl derivatives.

As is evident from FIG. 9, the body weight of the guinea pigs in the control was gradually lowered from the initiation of the administration, while those with the present acyl derivatives or 2-O-α-D-monoglucopyranosyl-L-ascorbic acid remarkably increased their body weight from 3 to 4 days after initiation of the administration. The guinea pigs with 2-O-α-D-monoglucopyranosyl-L-ascorbic acid needed eight days until they recovered their maximum body weight before initiating the administration; while those with 6-Octa-AA-2G needed only six days. The data indicates that the present acyl derivatives exceed 2-O-α-D-monoglucopyranosyl-L-ascorbic acid with respect to an ability of exerting the physiological action inherent to L-ascorbic acid. According to the anatomic finding, the internal bleeding caused by scorbutus was clearly found in the control group, while there found no such an observation in the group with the present acyl derivatives and 2-O-α-D-monoglucopyranosyl-L-ascorbic acid. Excluding numeral data, both of the levels of L-ascorbic acid in the liver and blood were below a detectable level at their collections in the control group, while the guinea pigs in the group with the present acyl derivatives or 2-O-α-D-monoglucopyranosyl-L-ascorbic acid were recovered nearly to a normal level. The same was applied to the blood level of alkaline phosphatase; the level in the control group was far below the normal level, while the level of the guinea pigs in the group with the present acyl derivatives or 2-O-α-D-monoglucopyranosyl-L-ascorbic acid recovered almost to the normal level. The acyl derivatives except for 6-Octa-AA-2G gave the similar result as in 6-Octa-AA-2G.

The result of this experiment evidences that the present acyl derivatives can be administered to mammals with lesser side effects, and, when administered to living bodies, they promptly release L-ascorbic acid to exert the physiological action inherent to L-ascorbic acid.

The following Examples describe the use of the acyl derivatives according to the present invention.

EXAMPLE B-1

Bun

One hundred parts by weight of wheat flour, two parts by weight of yeast, five parts by weight of sugar, two parts by weight of "TREHASTER", a high trehalose content syrup with a trehalose content of 28% or higher, d.s.b., commercialized by Hayashibara Shoji, Inc., Okayama, Japan, 0.1 part by weight of a yeast food, and 0.1 part by weight of either of the acyl derivatives obtained by the methods in Examples A-1 to A-7. The mixture was kneaded with an adequate amount of water in the usual manner, fermented at 26° C. for two hours, aged for 30 min, and backed up to obtain seven types of buns.

The products are high-quality buns with a satisfactory texture, adequate elasticity, and mild sweetness.

EXAMPLE B-2

Bonbon

Five parts by weight of "TREHASTER", a high trehalose content syrup with a trehalose content of 28% or higher, d.s.b., 300 parts by weight of "TREHAOSE", a crystalline trehalose powder with a trehalose content of 98% or higher, d.s.b., commercialized by Hayashibara Shoji, Inc., Okayama, Japan, 115 parts by weight of water, and five parts by weight of either of the acyl derivatives obtained by the methods in Examples A-1 to A-7, were mixed, and the mixture was boiled until giving a Bx 70, cooled to 80°C., and then mixed with 40 parts by weight of a brandy, followed by shaping the mixture in the usual manner to obtain seven types of bonbons.

The products are high-quality bonbons which contain fine trehalose crystals, have a brandy-like taste and flavor, and have a lesser change during storing.

EXAMPLE B-3

Chocolate

Forty parts by weight of cacao paste, 10 parts by weight of cacao butter, and 50 parts by weight of "TREHAOSE", a crystalline trehalose powder with a trehalose content of 98% or higher, d.s.b., were passed through a refiner to lower the granule size of the contents, and the resulting mixture was placed in a conche and kneaded at 50° C. for two days and nights. During the kneading, 0.5 part by weight of lecithin, and 0.5 part by weight of either of the acyl derivatives obtained by the methods in Examples A-1 to A-7 were added to, sufficiently mixed with, and dispersed in the above kneaded mixture. Thereafter, the mixture thus obtained was adjusted to a temperature of 31° C. by a thermoregulator, poured into a mold just before solidifying, deaerated with a vibrator, and passed through a cooling tunnel at 10° C. for 20 min to solidify the contents. The solidified contents were removed from the mold to obtain seven types of products.

The products, substantially free of hygroscopicity, have a satisfactory color, gloss, and internal textures, and smoothly melt in the mouth to impart a high-quality sweetness, flavor, and taste.

EXAMPLE B-4

Instant Corn Potage Soup

Thirty parts by weight of pregelatinized corn powder, five parts by weight of pregelatinized starch, four parts by weight of pregelatinized potato starch, 12 parts by weight of pregelatinized waxy corn starch, seven parts by weight of sodium chloride, seven parts by weight of "TREHAOSE", a crystalline trehalose powder with a trehalose content of 98% or higher, d.s.b., commercialized by Hayashibara Shoji, Inc., Okayama, Japan, 0.5 part by weight of onion powder, and 0.5 part by weight of either of the acyl derivatives obtained by the methods in Examples A-1 to A-7 were mixed and ground. To the mixture was added a solution prepared by melting by heating 0.5 part by weight of sorbitan fatty acid ester and nine parts by weight of plant hardened oil, and the resulting mixture was placed in a fluidized-bed granulator, granulated under spraying with a small amount of water, dried with air heated to 70° C., and sieved to obtain seven types of an instant corn potage soup with a lesser content of salt.

When poured into hot water, the products easily disperse into soups with a satisfactory flavor and taste. Since the products contain a lesser amount of sodium chloride, they are suitably used as foods for patients suffering from circulatory diseases, health foods for preventing life-style related diseases, and foods for maintaining and promoting the health.

EXAMPLE B-5

Egg Yolk Powder

Egg yolks prepared from fresh eggs were sterilized by a plate-type sterilizer at a temperature of 60–64° C. To one part by weight of the resulting liquid egg yolk were added four parts by weight of anhydrous crystalline trehalose powder, and 0.5 part by weight of either of acyl derivatives obtained by the methods in Examples A-1 to A-7. The mixtures thus obtained were blocked and pulverized in the usual manner to obtain seven types of egg yolk powders.

The products can be arbitrarily used as materials for confectionery such as premixes, ices, sherbets, ice creams, and emulsifiers; foods for infants and therapeutic nutritions such as orally-usable liquid foods and liquid-intubation-feedings; and traumatic therapeutics because the products have an anti-inflammatory action.

EXAMPLE B-6

Hair Rinse

One part by weight of "TREHAOSE", a crystalline trehalose powder with a trehalose content of 98% or higher, d.s.b., commercialized by Hayashibara Shoji, Inc., Okayama, Japan, two parts by weight of either of acyl derivatives obtained by the methods in Examples A-1 to A-7, two parts by weight of "αG RUTIN", α-glycosyl rutin commercialized by Toyo Sugar Refining Co., Ltd., Tokyo, Japan, two parts by weight of distearyl methylammonium chloride, two parts by weight of cetanol, two parts by weight of silicone oil, and one part by weight of polyoxyethylene oleyl alcohol ether, and an adequate amount of a flavor were dissolved by heating. To the mixture were added three parts by weight of 1,3-butylene glycol, 89 parts by weight of refined water, and an adequate amount of an antiseptic, followed by mixing the resulting mixture under stirring conditions and then cooling the contents to obtain seven types of hair rinses.

The product is satisfactorily used to promote the growth and regeneration of human and animal hairs and furs, and to treat/prevent dandruff, itchiness, and depilation.

EXAMPLE B-7

Milks Lotion

According to what is done conventionally, 0.5 part by weight of polyoxyethylene behenyl ether, one part by weight of polyoxyethylene sorbitol tetraoleate, one part by weight of glyceryl monostearate, lipophilic, 0.5 part by weight of pyruvic acid, 0.3 part by weight of behenyl alcohol, 0.2 part by weight of maltitol, one part by weight of avocado oil, one part by weight of either of acyl derivatives obtained by the methods in Examples A-1 and A-7, and adequate amounts of vitamin E and an antiseptic were dissolved by heating. To the mixture were added one part by weight of sodium L-lactate, five parts by weight of 1,3-butylene glycol, 0.1 part by weight of carboxyvinylpolymer, and 85.3 parts by weight of refined water were emulsified by a homogenizer. The resulting mixture was admixed with an adequate amount of a flavor and mixed while stirring to obtain seven types of milky lotions.

The products, having a lesser stickiness to the skin and a satisfactory extensibility, can be suitably used as sunburn preventives, skin-beautifying agents, and skin-whitening agents.

EXAMPLE B-8

Bath Salts

Twenty-one parts by weight of DL-sodium lactate, eight parts by weight of sodium pyruvate, five parts by weight of either of acyl derivatives obtained by the methods in Examples A-1 to A-7, and 40 parts by weight of ethanol were mixed with 26 parts by weight of refined water and adequate amounts of a color and a flavor to obtain seven types of bath salts.

In use, the products are diluted 10–10,000 times with hot water in bath tab. Since the products have a skin-beautifying and skin-whitening actions, they can be diluted with water for use as lotions and liquids for washing face.

EXAMPLE B-9

Tooth Paste

According to what is done conventionally, seven types of pastes were obtained by incorporating 0.1 part by weight of either of acyl derivatives, obtained by the methods in Examples A-1 to A-7, into 45 parts by weight of calcium secondary phosphate, 2.9 parts by weight of pullulan, 1.5 parts by weight of sodium lauryl sulfate, 20 parts by weight of glyceride, 0.5 part by weight of polyoxyethylene sorbitan laurate, 10 parts by weight of sorbitol, seven parts by weight of maltitol, and an adequate amount of refined water.

The products can be advantageously used as a tooth paste because they have an antiseptic activity and a satisfactory stability.

EXAMPLE B-10

Ointment

According to what is done conventionally, one part by weight of sodium acetate, trihydrate, four parts by weight of calcium DL-lactate, and 10 parts by weight of glycerine were mixed to homogeneity, and the mixture was mixed to homogeneity with 0.5 part by weight of peppermint oil, 50 parts by weight of petrolatum, 10 parts by weight of Japan wax, 10 parts by weight of lanolin, 14.5 parts by weight of sesame oil, and one part by weight of either of acyl derivatives, obtained by the methods in Examples A-1 to A-7, were mixed to homogeneity to obtain seven types of ointments.

The products, having a satisfactory skin permeability and extensibility and an effective therapeutic action on trauma, can be used as sun screens, skin-beautifying agents, and skin-whitening agents.

EXAMPLE B-11

Liquids

According to what is done conventionally, 1.8 parts by weight of boric acid and 0.005 part by weight of benzalkonium chloride or benzyldimethyltetradecylammonium chloride were mixed with adequate amounts of diluted hydrochloric acid, sodium hydroxide, and refined water, together with 0.05 part by weight of either of acyl derivatives obtained by the methods in Examples A-1 to A-7. The mixture was sterilized by filtering into seven types of liquids.

The products having a satisfactory permeability to eye mucosas can be effectively used as eye drops.

As described above, the present invention was made based on the finding of novel acyl derivatives of glycosyl-L-ascorbic acids. The acyl derivatives have a higher oil-solubility than L-ascorbic acid, glycosyl-L-ascorbic acids, and conventional inorganic esters of L-ascorbic acid such as phosphates and sulfates of L-ascorbic acid. Unlike conventional fatty acid esters of L-ascorbic acid such as those of stearates and palmitates, the present acyl derivatives release L-ascorbic acid in vivo. Comparing with L-ascorbic acid, the present acyl derivatives have an extremely higher stability to heat, light, oxygen, and metal ions, and the permeability to skins and mucosas. Similar to L-ascorbic acid, the present acyl derivatives have a property of entrapping radicals formed in vivo. Thus, the present acyl derivatives can be arbitrarily used as stable sources of L-ascorbic acid with lesser side effects in food products, cosmetics, and pharmaceuticals that need the physiological actions of L-ascorbic acid.

When used in food products, cosmetics, and pharmaceuticals which contain aqueous- and oil soluble-components, the present acyl derivatives function as surfactants and exert an activity of harmonizing the components to stabilize the whole contents because the acyl derivatives have both hydrophilic and hydrophobic parts within their molecules. Therefore, the acyl derivatives according to the present invention can be arbitrarily used in products, which utilize the properties of the acyl derivatives of L-ascorbic acid and/or intact L-ascorbic acid, for example, antioxidants, stabilizers, masking agents for unfavorable taste, buffers, emulsification accelerators, and ultraviolet absorbents, as well as reaction materials, reaction intermediates, and chemical reagents in the field of chemicals.

The present invention having these outstanding effects is a significant invention that greatly contributes to this art.

While there has been described what is at present considered to be the preferred embodiments of the invention, it will be understood the various modifications may be made therein, and it is intended to cover in the appended claims all such modifications as fall within the true spirits and scope of the invention.

We claim:

1. A 6-acyl derivative of a 2-glycosyl-L-ascorbic acid into which has been introduced an acyl group of RCO— wherein R represents a saturated or unsaturated straight or branched $C_2$–$C_{19}$ alkyl group.

2. The acyl derivative according to claim 1, which is a member selected from the group consisting of 2-glucopyranosyl-L-ascorbic acids and 2-galactopyranosyl-L-ascorbic acids.

3. The acyl derivative according to claim 1, which is a member selected from the group consisting of 6-O-butyryl-2-O-α-D-monoglucopyranosyl-L-ascorbic acid, 2-O-α-D-monoglucopyranosyl-6-O-hexanoyl-L-ascorbic acid, 2-O-α-D-monoglucopyranosyl-6-O-octanoyl-L-ascorbic acid, 6-O-decanoyl-2-O-α-D-monoglucopyranosyl-L-ascorbic acid, 6-O-dodecanoyl-2-O-α-D-monoglucopyranosyl-L-ascorbic acid, and mixtures thereof.

4. The acyl derivative according to claim 1, wherein said acyl group has a fatty acid as a base skeleton, wherein the acyl group has a parent acid selected from the group consisting of propionic acid, butyric acid, isobutyric acid, n-valeric acid, isovaleric acid, trimethyl acetate, caproic acid, n-heptanoic acid, caprylic acid, pelargonic acid, n-capric acid, lauric acid, myristic acid, palmitic acid, palmitoleic acid, stearic acid, oleic acid, ricinoleic acid, arachidic acid, petroselinic acid, vaccenic acid, linoleic acid, linolenic acid, eleostearic acid, licanic acid, parinaric acid, tariric acid, gadoleic acid, and arachidonic acid.

5. A cosmetic composition comprising an acyl derivative of claim 1.

6. The cosmetic composition according to claim 5, which contains at least 0.005 w/w % said acyl derivative.

7. The cosmetic composition according to claim 5, which further comprises an α-glycosyl bioflavonoid.

8. The cosmetic composition according to claim 7, which contains an about 0.001–10 w/w % of said α-glycosyl bioflavonoid.

9. A process for producing said acyl derivative of claim 1, comprising the step of reacting a glycosyl-L-ascorbic acid with an acylating agent.

10. The process according to claim 9, wherein said glycosyl-L-ascorbic acid is reacted with said acylating agent in a nonaqueous system.

11. The process according to claim 9, wherein said acylating agent is a member selected from the group consisting of acid halides and acid anhydrides.

12. The process according to claim 11, wherein said acid halides and acid anhydrides are members selected from the group consisting of carboxylic halides and carboxylic acid anhydrides.

13. The process according to claim 9, wherein said acylating agent is a lower or higher fatty acid anhydride, said anhydride having a parent fatty acid selected from the group consisting of propionic acid, butyric acid, isobutyric acid, n-valerianic acid, isovaleric acid, trimethyl acetate, caproic acid, n-heptanoic acid, caprylic acid, pelargonic acid, n-capric acid, lauric acid, myristic acid, palmitic acid, palmitoleic acid, stearic acid, oleic acid, ricinoleic acid, arachidic acid, petroselinic acid, vaccenic acid, linoleic acid, linolenic acid, eleostearic acid, licanic acid, Darinaric acid, tariric acid, gadoleic acid, and arachidonic acid.

14. The process according to claim 13, wherein said acylating agent is a member selected from the group consisting of $C_3$–$C_{20}$ carboxylic halides and $C_3$–$C_{20}$ carboxylic acid anhydrides.

15. The derivative according to claim 9, wherein said glycosyl-L-ascorbic acid is a member selected from the group consisting of 2-glucopyranosyl-L-ascorbic acids, and 2-galactopyranosyl-L-ascorbic acids.

16. The process according to claim 9, wherein one mole of said glycosyl-L-ascorbic acid is reacted with not higher than three moles of said acylating agent.

17. A pharmaceutical composition, comprising said acyl derivative of claim 1 as an active ingredient in a pharmaceutically acceptable carrier.

18. A food product comprising an acyl derivative of claim 1.

19. The food product according to claim 18, which contains at least 0.01 w/w % of said acyl derivative.

* * * * *